United States Patent
Matsui et al.

(10) Patent No.: US 9,393,562 B2
(45) Date of Patent: Jul. 19, 2016

(54) ANALYZER

(75) Inventors: Takuya Matsui, Mito (JP); Ryoji Inaba, Hitachinaka (JP); Kazumichi Imai, Hitachinaka (JP); Ryusuke Kimura, Hitachinaka (JP)

(73) Assignee: HITACHI HIGH-TECHNOLOGIES CORPORATION, Tokyo (JP)

(*) Notice: Subject to any disclaimer, the term of this patent is extended or adjusted under 35 U.S.C. 154(b) by 429 days.

(21) Appl. No.: 13/983,340

(22) PCT Filed: Jan. 13, 2012

(86) PCT No.: PCT/JP2012/050556
§ 371 (c)(1),
(2), (4) Date: Aug. 2, 2013

(87) PCT Pub. No.: WO2012/111366
PCT Pub. Date: Aug. 23, 2012

(65) Prior Publication Data
US 2013/0316336 A1 Nov. 28, 2013

(30) Foreign Application Priority Data
Feb. 18, 2011 (JP) ................. 2011-033730

(51) Int. Cl.
*C12Q 1/68* (2006.01)
*B01L 3/00* (2006.01)
(Continued)

(52) U.S. Cl.
CPC .............. *B01L 3/502* (2013.01); *C12Q 1/6869* (2013.01); *G01N 35/1095* (2013.01);
(Continued)

(58) Field of Classification Search
CPC ........... B01L 3/502; B01L 2400/0406; B01L 3/0224; B01L 2300/026; G01N 35/1004; G01N 35/0098
See application file for complete search history.

(56) References Cited

U.S. PATENT DOCUMENTS 5,443,792 A 8/1995 Buhler
5,512,247 A 4/1996 Bonacina et al.
(Continued)

FOREIGN PATENT DOCUMENTS

JP 2-8746 1/1990
JP 5-346433 12/1993
(Continued)

OTHER PUBLICATIONS

JP Office Action of Appln. No. 2011-033730 dated Dec. 9, 2014 with English translation.
(Continued)

*Primary Examiner* — Krishnan S Menon
*Assistant Examiner* — Dwan A Gerido
(74) *Attorney, Agent, or Firm* — Baker Botts L.L.P.

(57) ABSTRACT

Provided is an analyzer capable of reducing the amount of wasted reagents and shortening time required for solution sending, thus increasing throughput for analysis. A microsyringe sucks a minimum required amount of reagent that is substantially the same amount of capacity of a flow cell to a sampling nozzle. Then, the sampling nozzle is inserted into an injection port of the flow cell, and the reagent is injected into the flow cell by driving the microsyringe. The inside of the sampling nozzle is cleaned by moving the sampling nozzle to the cleaning tank and ejecting cleaning water from the sampling nozzle, and the outside of the sampling nozzle is cleaned by spraying cleaning water from an inner wall of the cleaning tank.

10 Claims, 12 Drawing Sheets

(51) Int. Cl.
 *B01L 3/02* (2006.01)
 *G01N 35/10* (2006.01)
 *G01N 35/00* (2006.01)

(52) U.S. Cl.
 CPC ......... *B01L 3/0224* (2013.01); *B01L 2300/026* (2013.01); *B01L 2400/0406* (2013.01); *G01N 35/0098* (2013.01); *G01N 35/1002* (2013.01); *G01N 35/1004* (2013.01); *G01N 2035/1039* (2013.01)

(56) References Cited

U.S. PATENT DOCUMENTS

| | | |
|---|---|---|
| 6,293,750 B1 | 9/2001 | Cohen et al. |
| 2003/0128043 A1 | 7/2003 | Zeltz et al. |
| 2003/0152957 A1 | 8/2003 | Shinohara et al. |
| 2004/0141880 A1 | 7/2004 | Handler et al. |

FOREIGN PATENT DOCUMENTS

| | | |
|---|---|---|
| JP | 8-43403 | 2/1996 |
| JP | 2000-52288 | 2/2000 |
| JP | 2003-185664 | 7/2003 |
| JP | 2003-520972 | 7/2003 |
| JP | 2003-232791 | 8/2003 |
| JP | 2004-163408 | 6/2004 |
| JP | 2008-528040 | 7/2008 |
| JP | 2009-300152 | 12/2009 |
| JP | 2011-33551 | 2/2011 |
| WO | 01/54814 A2 | 8/2001 |
| WO | 2006/084132 A2 | 8/2006 |

OTHER PUBLICATIONS

JP Office Action of Appln. No. 2011-033730 dated May 7, 2014 with English translation.

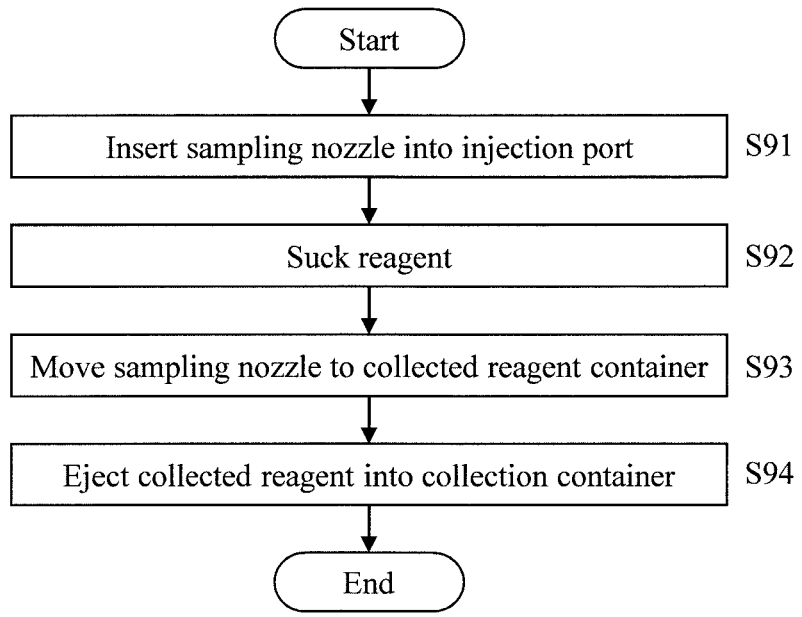
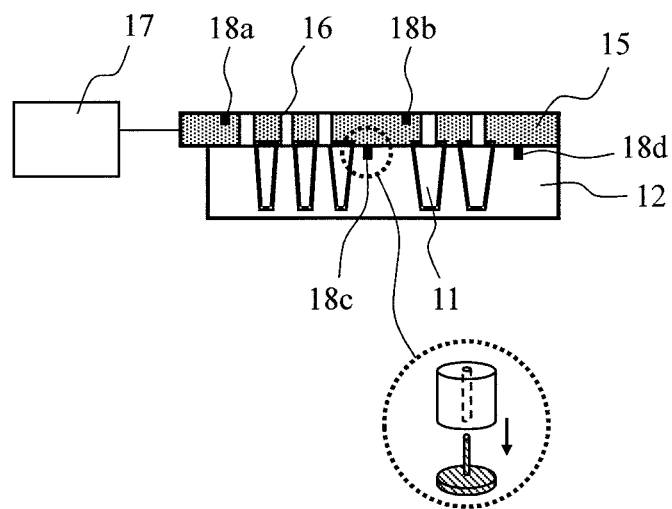

ANALYZER

TECHNICAL FIELD

The present invention relates to an analyzer configured to inject a reagent into a flow cell including a sample immobilized thereto and detect a reaction generated in the flow cell for analysis of the sample.

BACKGROUND ART

To determine the base sequence of DNA or RNA, a method based on electrophoresis has been mainly used. This method includes the steps of preparing a cDNA fragment sample synthesized in advance via a reverse transcription reaction of a DNA fragment or a RNA sample for sequencing, for which a dideoxy reaction based on the well-known Sanger method is performed, followed by electrophoresis, thus measuring its molecular weight separation/expansion pattern for analysis. Meanwhile, a recently developed method called a next-generation DNA sequencer performs the steps of immobilizing a large number of DNA fragments as a sample to a substrate and determining information on the sequence of these fragments in parallel.

Such a next-generation DNA sequencer places a lot of beads, to which DNA fragments as a sample are immobilized, in a flow cell as a reaction field. Then, a reagent is supplied to the flow cell, and fluorescent signals generated due to an elongation reaction of bases are detected, based on which the base sequence of the sample is analyzed. Many of these next-generation DNA sequencers use a solution sending system including a tube and a valve to supply a reagent. Specifically, the system includes a tube making up a supply passage of each reagent and another tube connected to a flow cell as well as a valve placed therebetween, and switches the valves, thus supplying a desired reagent to the flow cell.

CITATION LIST

Patent Literature

Patent Literature 1: JP 2008-528040 A

SUMMARY OF INVENTION

Technical Problem

The solution sending system configured to change a type of a reagent sent via a tube by a switching valve and inject the reagent to a flow cell has the following problems.

1. It takes time to send solution.
A longer tube means longer time to send solution.
2. Reagents may mix (contamination) in the tube.
Since a plurality of reagents flow through the same passage, a tube inside of which is not cleaned enough may generate contamination. The amount of cleaning liquid cleaning the inside of a tube also increases directly with the length of the tube.
When two types of reagents are successively sent, since the flow velocity distribution of these reagents becomes parabolic and not plug, they will be mixed more as the passage becomes longer. These two types of reagents may be sent while sandwiching air therebetween so as to suppress the mixture thereof. However, a longer tube inevitably causes diffusion of reagents, and so causes the mixture thereof.
3. Extra amount of reagents is required, and so the accuracy of dispensing deteriorates.
Since the reagents are mixed in a tube, the reagents in the amount more than the capacity of the flow cell have to be sent to the flow cell to inject the reagent that is not mixed only for reaction.
4. Since a user has to change a tube, the system needs maintenance.
5. Contamination occurs in a switching valve that is difficult to clean.

Some types of the next-generation DNA sequencers use expensive reagents, and so reduction in the amount of wasted reagents that do not contribute to the reaction has been demanded. In order to lengthen the reading base length, the mixture of reagents has to be minimized. It is also requested to shorten the time required for solution sending to increase throughput of analysis.

It is an object of the present invention to provide an analyzer capable of meeting such requirements.

Solution to Problem

An analyzer according to the present invention includes: a reagent rack installation part where a reagent rack holding a plurality of reagent containers is to be installed; a flow cell installation part where a flow cell including an internal passage as well as an injection port and a discharge port connected to the internal passage is to be installed; a sampling nozzle; a liquid level detection unit that detects the sampling nozzle coming into contact with a liquid level; a cleaning tank; a nozzle driving mechanism that drives the sampling nozzle among the reagent containers, the cleaning tank and the injection port of the flow cell; a detection unit that detects a change in a sample in the flow cell; a solution sending system; and a controller that controls various parts of the analyzer.

The solution sending system includes: a cleaning liquid tank containing cleaning liquid; a microsyringe connected to the sampling nozzle, the microsyringe being for suction and ejection of liquid to/from a tip end of the sampling nozzle; a first mechanism to send cleaning liquid from the cleaning liquid tank to the microsyringe; and a second mechanism to send cleaning liquid from the cleaning liquid tank to the cleaning tank.

The controller controls the microsyringe while inserting the sampling nozzle into a reagent by a predetermined distance in response to detection by the liquid level detection unit of a surface of the reagent in the reagent container, thus sucking a required amount of the reagent from the reagent container ahead of a part of the sampling nozzle filled with cleaning liquid, controls the microsyringe while inserting the sampling nozzle into the injection port of the flow cell, thus injecting the sucked reagent into the flow cell through the injection port, or operates the first mechanism and/or the second mechanism while positioning the sampling nozzle in the cleaning tank, thus cleaning an inside and/or an outside of the sampling nozzle.

The first mechanism and the second mechanism can be implemented by various means. For instance, the first mechanism and the second mechanism can be configured with a syringe including a pair of valves disposed on the upstream and the downstream, each of which is openable/closable and is controlled so that one of them is in an open state and the other is in a closed state. Alternatively, when the analyzer includes a cleaning liquid circulation passage, through which cleaning liquid is sucked from a cleaning liquid tank and is returned to the cleaning liquid tank again, the first mechanism may be configured with the cleaning liquid circulation passage and a valve provided in a passage connecting the cleaning liquid circulation passage and the microsyringe. Then, the second mechanism may be configured with the cleaning liquid circulation passage and a valve provided in a passage connecting the cleaning liquid circulation passage and the cleaning tank.

As the amount of a reagent sucked from the reagent container to the sampling nozzle, capacity of the flow cell or more and an amount obtained by adding 10 µL to the capacity of the flow cell or less suffice, and so the usage of a reagent can be minimized.

The analyzer may include a plurality of members enabling the liquid level detection unit to detect the sampling nozzle coming into contact at positions where the sampling nozzle is accessible, such as a top face of the reagent rack. These members may be used as members to allow the nozzle driving mechanism to perform driving calibration of the sampling nozzle.

The nozzle driving mechanism, as one example, includes: a guide rail; a movement unit that moves linearly along the guide rail; and an arm, to which the sampling nozzle is fixed, the arm rotating about a rotating shaft set at the movement unit. The members for driving calibration of the sampling nozzle may include at least two members that are disposed at a known interval in a direction along the guide rail, and at least two members that are disposed at a known interval in a direction orthogonal to the guide rail.

The controller may have a function of calibration of a position of the sampling nozzle by detecting positions of the members for calibration using the liquid level detection unit. During execution of the calibration function, the controller detects positions of at least two members disposed in the direction along the guide rail and finds, based on a driving signal to the nozzle driving mechanism and a distance between the two members, a linear movement coefficient that is a ratio between a traveling distance in the linear movement direction and the driving signal. The controller detects a position of each of at least two members having different distances in the direction orthogonal to the guide rail from two directions and finds, based on a driving signal to the nozzle driving mechanism and the linear movement coefficient found before, a rotating radius of a tip end of the sampling nozzle about the rotating shaft and a rotary movement coefficient that is a ratio of a rotating angle and the driving signal. The controller further detects two members disposed at a known interval in the direction orthogonal to the guide rail, and finds, based on a driving signal to the nozzle driving mechanism, the linear movement coefficient and the rotary movement coefficient found before, a rotating angle of the arm detecting the members. The thus found parameters enable precise positioning of the sampling nozzle at a desired position.

An analysis method according to the present invention includes the steps of: moving a sampling nozzle filled with cleaning liquid to a tip end thereof to above a reagent container containing a reagent; moving the sampling nozzle downward; in response to detection by liquid level detection means of a surface of the reagent in the reagent container, inserting the sampling nozzle into the reagent by a predetermined distance and stopping descending of the sampling nozzle; sucking a required amount of the reagent into the sampling nozzle; moving the sampling nozzle to a cleaning tank; spraying cleaning liquid to a surface of the sampling nozzle in the cleaning tank, thus cleaning and removing the reagent attached to an outside of the sampling nozzle; moving the sampling nozzle to above an injection port of a flow cell; moving the sampling nozzle downward, and inserting the tip end of the sampling nozzle into the injection port; injecting under pressure the reagent sucked at the sampling nozzle to the flow cell; after the injecting under pressure, keeping the sampling nozzle inserted into the injection port for predetermined duration; subsequently removing the sampling nozzle from the injection port and moving the sampling nozzle upward; moving the sampling nozzle to the cleaning tank; ejecting the cleaning liquid from the sampling nozzle in the cleaning tank, thus cleaning an inside of the sampling nozzle, while spraying the cleaning liquid to the outside of the sampling nozzle for cleaning; moving the sampling nozzle to above the injection port of the flow cell; moving the sampling nozzle downward and inserting the tip end of the sampling nozzle into the injection port; injecting the cleaning liquid from the sampling nozzle into the flow cell, thus rinsing off unreacted reagent; and taking an image of the flow cell, thus detecting a change due to the injection of the reagent. As the cleaning liquid used in the step of rinsing off the unreacted reagent from the flow cell, some type of reagent may be used, and instead, cleaning liquid to clean the sampling nozzle, e.g., pure water may be used. When a reagent is used as the cleaning liquid, such cleaning liquid (reagent) also may be placed on the reagent rack, and may be injected into the flow cell by a method similar to that for other reagents.

Prior to rinsing off the unreacted reagent: the method may further include the steps of: inserting the sampling nozzle into the injection port of the flow cell and sucking the reagent in the flow cell; moving the sampling nozzle to above a collected reagent container; and ejecting the sucked reagent to the collected reagent container. Thereby, the reagent can be collected from the flow cell for reuse.

Advantageous Effects of Invention

The present invention can minimize the usage of reagents and can shorten time required for solution sending, thus increasing throughput for analysis.

Problems, configurations, and advantageous effects other than those explained above will be made apparent by the following explanation of embodiments.

BRIEF DESCRIPTION OF DRAWINGS

FIG. 13 is a flowchart showing procedure to collect a reagent.

FIG. 14 is a schematic cross-sectional view showing another embodiment of the reagent rack.

DESCRIPTION OF EMBODIMENTS

The following describes embodiments of the present invention, with reference to the drawings. The present invention is generally applicable to an analyzer of a type that analyzes a sample by injecting the sample into a flow cell and observing the result, and the following describes an example where the present invention is applied to a DNA sequencer.

Figure 1A:
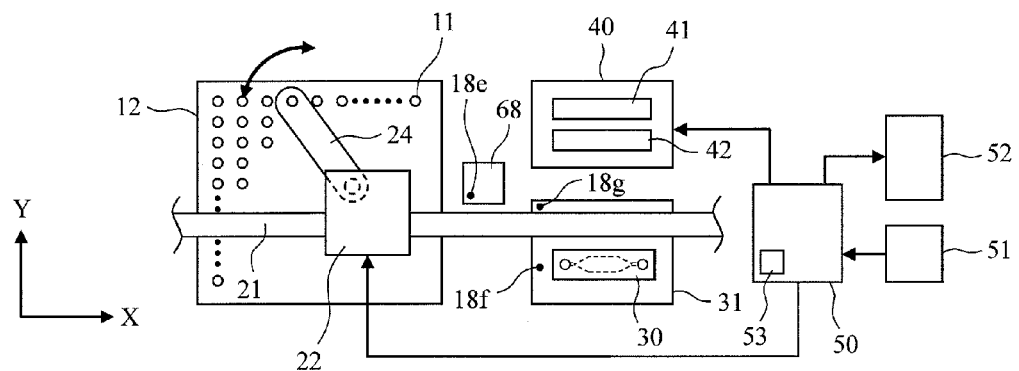
FIG. 1A is a schematic plan view showing an exemplary analyzer according to the present invention.
Figure 1B:
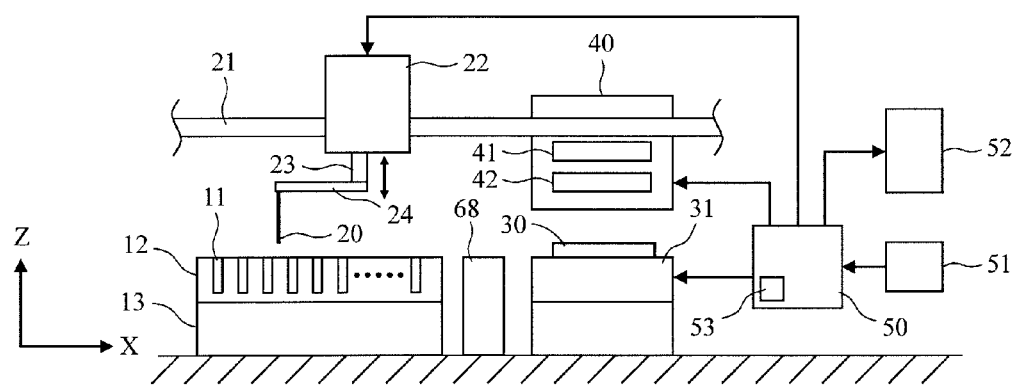
FIG. 1B is a schematic front view showing an exemplary analyzer according to the present invention.

FIGS. 1A and 1B schematically show an analyzer (DNA sequencer) according to the present invention, where FIG. 1A is a schematic plan view and FIG. 1B is its schematic front view. XYZ axes are set as illustrated in the drawings for the description.

The analyzer of the present embodiment includes: a reagent rack base 13, on which a reagent rack 12 holding a plurality of reagent containers 11 is placed; a flow cell stage 31 that is movable while holding one or more flow cells 30; a sampling nozzle 20 capable of sucking and ejecting liquid from its tip end; a nozzle driving mechanism that drives the sampling nozzle 20 to a desired three-dimensional position; a cleaning tank 68 that cleans the sampling nozzle 20; and a detection unit 40 that detects a change generated at the sample in the flow cell 30 when the reagent is injected thereto. Suction and ejection of a sample by the sampling nozzle 20 and cleaning are performed by a solution sending system not illustrated. The solution sending system is described in detail, with reference to FIG. 2.

Various parts of the analyzer are under the control of a control/operation unit 50, and the control/operation unit 50 controls the analyzer in accordance with a program set at the control/operation unit 50 via an input unit 51 for continuous operation. The control/operation unit 50 includes a memory that stores information such as the analysis procedure, the coordinates position of the plurality of reagent containers 11 placed at the reagent rack 12 and the cleaning tank 68, types of reagents contained in the reagent containers, the coordinates position of the injection port to inject a reagent and cleaning liquid to the flow cell 30, and processing procedure of a detection result by the detection unit 40. The control/operation unit 50 controls various parts of the analyzer in accordance with an analysis program while referring to the information stored in the memory, thus executing the analysis.

Figure 4:
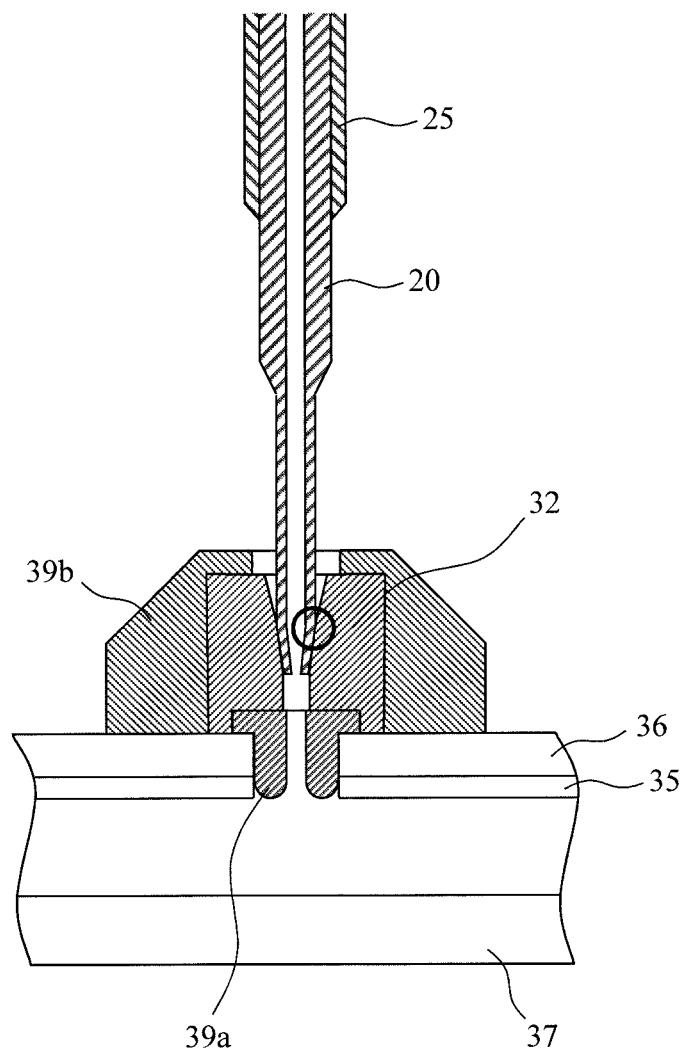
FIG. 4 explains an injection port of a flow cell.

As one example, the sampling nozzle 20 is a hollow nozzle made of a metal material, e.g., SUS, having an outer diameter of 1 mm and an inner diameter of 0.5 mm at its tip end and a length of about 150 mm, and the sampling nozzle 20 is connected to a solution sending system described later to suck, at its tip end, a necessary amount of a reagent from a desired reagent container 11 placed at the reagent rack 12 and eject the reagent to the flow cell 30 or the like. The sampling nozzle 20 further is made of a material and has a structure suitable for liquid level detection. The liquid level detection is executed by a level detection unit 53 provided in the control/operation unit 50 using a known method for liquid level detection detecting a change in capacitance when the sampling nozzle 20 made of metal comes into contact with a conductive region such as a liquid level. A liquid level detection signal output from the liquid level detection unit 53 is subsequently used to control the device. As shown in FIG. 4, metal is exposed at the tip end of the sampling nozzle 20, and in order to avoid malfunction for liquid level detection, the upper part of the sampling nozzle 20 is coated with a water-repellent resin layer 25.

The nozzle driving mechanism includes: a guide rail 21; a linear movement unit 22 that moves linearly along the guide rail 21 in the X-axis direction; and an arm 24 that is rotatable around a rotating shaft 23 provided at the linear movement unit 22. The sampling nozzle 20 is fixed at a part of the arm 24 on the opposite side of the rotating shaft 23. The linear movement unit 22 includes a pinion meshing with a rack provided at the guide rail 21, for example, and the rotary driving of the pinion by a stepping motor enables movement of the linear movement unit 22 to a desired position in the X-axis direction. The rotating shaft 23 similarly rotates by a stepping motor in the X-Y plane, and moves vertically in the Z-axis direction so as to position the tip end of the sampling nozzle 20 at a desired Z-axis direction position. Combining the linear movement in the X-axis direction, the rotary movement about the rotating shaft 23 and the vertical movement in the Z-axis direction by the nozzle driving mechanism allows the sampling nozzle 20 to access any reagent container 11 placed at the reagent rack 12, the cleaning tank 68 and an injection port of the flow cell described later.

The detection unit 40 includes a light source 41 to irradiate the flow cell with light and an imaging device 42, such as a CCD, capable of performing color separation of fluorescence emitted from the flow cell 30 irradiated with excitation light for detection. The flow cell 30 can move in the X, Y-axis directions by the flow cell stage 31. During the operations such as reagent injection and cleaning via the sampling nozzle 20, the flow cell 30 is placed away from below the detection unit 40 as shown in the drawing, and before the detection by the detection unit 40, the flow cell 30 is moved by the flow cell stage 31 to the place below the detection unit 40.

A display unit 52 displays information such as input information input from the input unit 51, information on the analysis procedure such as an image shot by the detection unit 40, information such as a current device state and device parameters, information on the completed steps in the entire process of analysis, and an analysis result.

Figure 2:
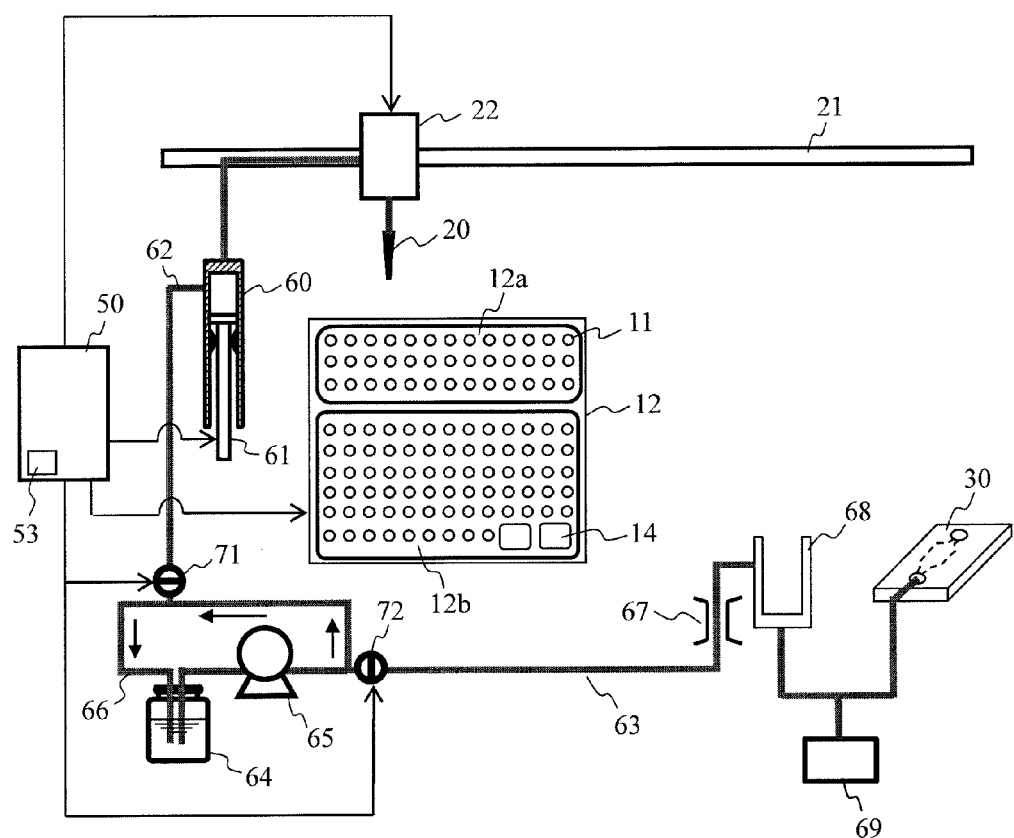
FIG. 2 schematically shows an exemplary solution sending system.

FIG. 2 schematically shows an exemplary solution sending system incorporated in the analyzer of the present embodiment. This solution sending system implements sucking and ejecting of a reagent from the tip end of the sampling nozzle 20 and cleaning of the sampling nozzle 20.

The solution sending system of the present embodiment includes: a microsyringe 60 to suck/eject a reagent while weighing it from the tip end of the sampling nozzle 20; and a first passage 62 and a second passage 63 to supply cleaning liquid to the sampling nozzle 20 and the cleaning tank 68, respectively. In the present embodiment, cleaning liquid stored in a cleaning liquid tank 64 is sucked by a pump 65 that is continuously operated, and is returned to the cleaning liquid tank 64 via a cleaning liquid circulation passage 66. That is, cleaning liquid is always circulated by the pump 65 in the direction of the arrows along the cleaning liquid circulation passage 66. The first passage 62 has one end connected to the cleaning liquid circulation passage 66 via a first electromagnetic valve 71 and has the other end that communicates with the inside of the sampling nozzle 20 via the microsyringe 60. Similarly, the second passage 63 has one end connected to the cleaning liquid circulation passage 66 via a second electromagnetic valve 72 and has the other end that opens at a side wall of the cleaning tank 68. Exemplary cleaning liquid may include pure water.

The nozzle driving mechanism moves the tip end of the sampling nozzle 20 in the cleaning tank 68, and in this state, the first electromagnetic valve 71 only is turned open. Then, cleaning liquid that is sent under pressure from the pump 65 is sprayed from the sampling nozzle 20 to the inside of the cleaning tank 68, thereby cleaning the inside of the sampling nozzle 20. During the cleaning, a plunger 61 of the microsyringe 60 may move or not move. When the second electromagnetic valve 72 only is turned open, then cleaning liquid is sprayed from the inner wall of the cleaning tank 68, whereby the outside of the sampling nozzle 20 can be cleaned. When the first electromagnetic valve 71 and the second electromagnetic valve 72 are turned open at the same time, the inside and the outside of the sampling nozzle 20 can be cleaned at the same time in the cleaning tank 68. The open/close control of the first electromagnetic valve 71 and the second electromagnetic valve 72 is performed by the control/operation unit 50.

The ratio between cleaning liquid supplied to the sampling nozzle 20 via the first passage 62 and cleaning liquid supplied to the cleaning tank 68 via the second passage 63 is set by a flow amount regulator 67 provided at a position of the second passage 63 closer to the cleaning tank 68. Cleaning liquid after cleaning the sampling nozzle 20 is stored in a waste liquid tank 69. Cleaning liquid stored in the cleaning tank 68 can be stored in the waste liquid tank 69 by a waste liquid discharge pump not illustrated. Cleaning liquid can be sent from the cleaning liquid tank 64 as well by sealing the cleaning tank 68 and opening the second electromagnetic valve 72 and by drawing by the waste liquid discharge pump. Further, a similar operation following emptying the cleaning liquid tank 64 and then opening the first electromagnetic valve 71 can remove the liquid in the first passage 62, the second passage 63 and the cleaning liquid circulation passage 66. If the pump 65, the second electromagnetic valve 72 and piping are not connected correctly, since cleaning liquid does not flow from the cleaning tank 68, and so the sampling nozzle 20 cannot be cleaned. In this case, since the liquid level detection function of the nozzle does not operate, the error can be detected. A cleaning operation consumes the cleaning liquid in the cleaning liquid tank 64. Since the cleaning liquid tank 64 is provided with a liquid level sensor, if the amount of cleaning liquid in the cleaning liquid tank 64 becomes small, the cleaning liquid tank 64 is refilled with cleaning liquid from a cleaning liquid refilling tank provided separately and not illustrated.

In this way, the solution sending system of the present embodiment can supply a large amount of cleaning liquid to the inside or the outside of the sampling nozzle, or both of the inside and the outside of the sampling nozzle by a pump in a short time, and so can sufficiently clean a reagent attached to the sampling nozzle after operation in a short time. This can avoid contamination of reagents and can improve analysis accuracy. This further can shorten the cleaning duration and so can improve the throughput of the analysis.

The reagent rack 12 is provided with a temperature sensor and a temperature adjustment unit such as a Peltier device, thereby keeping the temperature of a reagent held at the reagent container 11 constant. For instance, a group of reagents held at a first region 12a of the reagent rack is kept at a room temperature, and a group of reagents held at a second region 12b is kept at 4° C. The temperature control of the reagent rack 12 also can be performed by the control/operation unit 50. Some types of reagents are desirably mixed with other reagents immediately before the use and are supplied to a flow cell. To this end, the reagent rack 12 is provided with a premixing container 14 to prepare a mixed reagent. For such a mixed reagent, reagents that are sucked by the sampling nozzle 20 from different reagent containers 11 are once ejected to the premixing container 14 for mixture in the premixing container 14. Then, such a prepared mixed reagent in the premixing container 14 is sucked by the sampling nozzle 20 again, and is supplied to the flow cell 30.

Figure 3A:
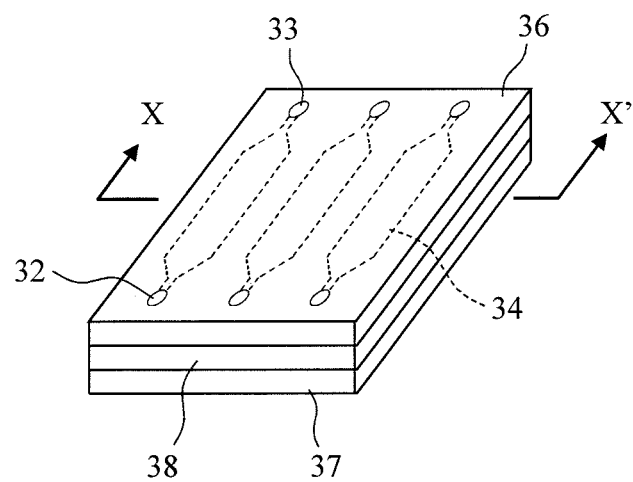
FIG. 3A is a schematic perspective view showing an exemplary flow cell.
Figure 3B:
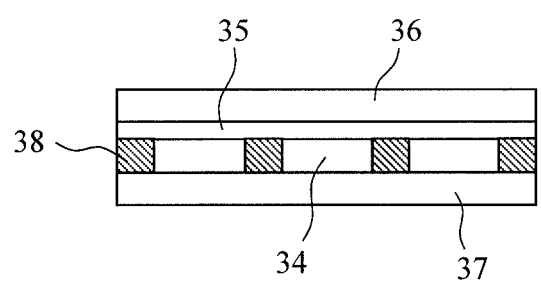
FIG. 3B is a cross sectional view taken along the line X-X' of FIG. 3A.

FIGS. 3A and 3B schematically show an exemplary flow cell. FIG. 3A is a perspective view of the flow cell, and FIG. 3B is a cross section taken along the line X-X' of FIG. 3A.

This exemplary flow cell includes an injection port 32 and a discharge port 33 as well as a passage 34, through which liquid flows. A flow cell for DNA sequencer is designed so as to include a carrier such as a bead having a nucleic acid sample on its surface or a free nucleic acid sample in the passage, and so is configured to include an upper substrate 36 including a sample immobilization layer 35, to which a carrier such as a bead having a nucleic acid sample on its surface or a free nucleic acid sample is bound, and a lower substrate 37. Between the upper substrate 36 and the lower substrate 37, the passage 34 is defined. The passage 34 functions as a passage through which a reagent necessary for a reaction for nucleic acid analysis is supplied and as a reaction chamber where the reaction takes place. In order to provide a space for the passage 34, a spacer 38 is disposed between the upper substrate 36 and the lower substrate 37. That is, the flow cell shown in FIGS. 3A and 3B has a structure such that the upper substrate 36, the spacer 38, a part of which is bored so as to correspond to the passage, and the lower substrate 37 are bonded. Reaction solution is injected from the injection port 32 and is discharged from the discharge port 33. In one example, the spacer has a thickness of 50 to 100 μm, the passage formed by boring the spacer has a width of 20 to 30 mm, and the passage has a length of 75 to 100 mm, and these numerical values are not restrictive.

The upper substrate 36 on the side facing the detection unit 40 is made of glass, quartz, sapphire or resins such as acrylic resin and cyclo olefin polymer, which are materials transmitting excitation light and fluorescence. The sample immobilization layer 35 is made of inorganic oxide. Exemplary inorganic oxide making up the immobilization layer may be selected from the group consisting of titania, zirconia, alumina, zeolite, vanadium pentoxide, silica, sapphire, tungsten oxide and tantalum pentoxide, or may be the mixture of at least two types of them. Among them, titania, zirconia, alumina, zeolite, vanadium pentoxide or the mixture of them are desirable. These inorganic oxides bind to a phosphoric acid part or an ester phosphate part in the nucleic acid sample molecule, thus enabling binding of the nucleic acid sample with the sample immobilization layer. Especially titania, zirconia, alumina, zeolite and vanadium pentoxide contain Lewis acid sites and Brønsted acid sites a lot, which have large electrophilicity and so are capable of binding with DNA.

After injecting aqueous solution including a carrier such as a bead having a nucleic acid sample on its surface or a free nucleic acid sample from the injection port 32, this is held for certain duration, thus immobilizing the nucleic acid on the sample immobilization layer 35. At this time, the carrier such as a bead having a nucleic acid sample on its surface or a free nucleic acid sample is immobilized on the sample immobilization layer 35 substantially uniformly. Then, aqueous solution of a compound selected from the group consisting of carboxylic compounds, phosphate compounds, sulfated compounds, nitrile compounds, salt thereof, and the mixture of at least two types of these compounds is similarly injected to form a blocking layer. These compounds are specifically bound to inorganic oxide, and so a region other than the binding part of the nucleic acid sample to the sample immobilization layer can be blocked in a state of a high coverage rate. The blocking layer can prevent infiltration of reaction solution to the binding part of the nucleic acid sample to the sample immobilization layer, which can prevent the nucleic acid sample from removing from the sample immobilization layer.

FIGS. 3A and 3B show an exemplary flow cell including three passages formed therein, and the number of passages is not limited to three. More passages in number mean more reactions taking place at one time, thus enabling high throughput analysis. A flow cell including a nucleic acid sample immobilized to an internal passage thereof is set at the flow cell stage of the analyzer for analysis of the nucleic acid. During analysis, the temperature of the flow cell is adjusted at a predetermined temperature by a temperature control unit provided at the flow cell stage.

FIG. 4 is a schematic cross-sectional view showing the sampling nozzle being inserted into an injection port of the flow cell.

The injection port 32 of the flow cell is made of peek resin, and has a tapered (conical shape) opening having an inner diameter of about 3 mm at the upper part and an inner diameter of about 1 mm at the lower part that is the same as the outer diameter of the tip end of the sampling nozzle 20. The injection port 32 is connected liquid-tightly to the upper substrate 36 of the flow cell via an O-ring 39a, and is fixed to the flow cell by a fixing member 39b covering a side face and an upper face at a shoulder part of the injection port. The sampling nozzle 20 descends from above and then is inserted to the injection port 32 until the tip end of the nozzle having a part slightly tapering down to the end comes into contact with the tapered part of the injection port 32 for sealing as indicated with a circle in the drawing.

The following describes the procedure of supplying a reagent to the flow cell for analysis from the state where the reagent rack 12 is placed at the reagent rack base 13 of the analyzer and the flow cell 30 is placed at the flow cell stage 31.

(1) Sampling Nozzle Cleaning

Figure 6:
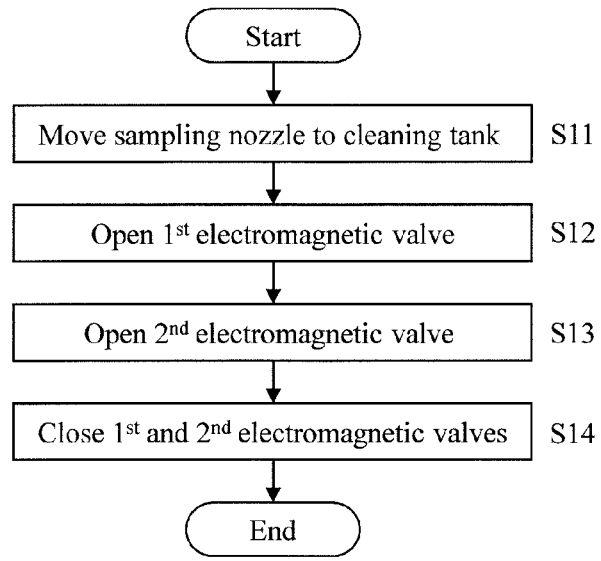
FIG. 6 is a flowchart showing exemplary control procedure to clean a sampling nozzle.

Firstly cleaning of the sampling nozzle 20 is performed. FIG. 6 shows the procedure of control by the control/operation unit 50.

The control/operation unit 50 firstly controls the nozzle driving mechanism to move the sampling nozzle 20 to the cleaning tank 68 (S11). Next the control/operation unit 50 controls the first electromagnetic valve 71 to be open, the first electromagnetic valve 71 being connected to the cleaning liquid circulation passage 66 where cleaning liquid is circulated by the pump 65 (S12). During the cleaning, the plunger 61 of the microsyringe 60 may move or not move. In this state, cleaning liquid that is sent under pressure from the pump 65 enters the microsyringe 60 via the first electromagnetic valve 71 and the first passage 62 and then flows through the sampling nozzle 20 and is sprayed from the tip end of the nozzle in the cleaning tank 68. In this way, the inside of the nozzle is cleaned. Pure water is used as the cleaning liquid.

Figure 5:
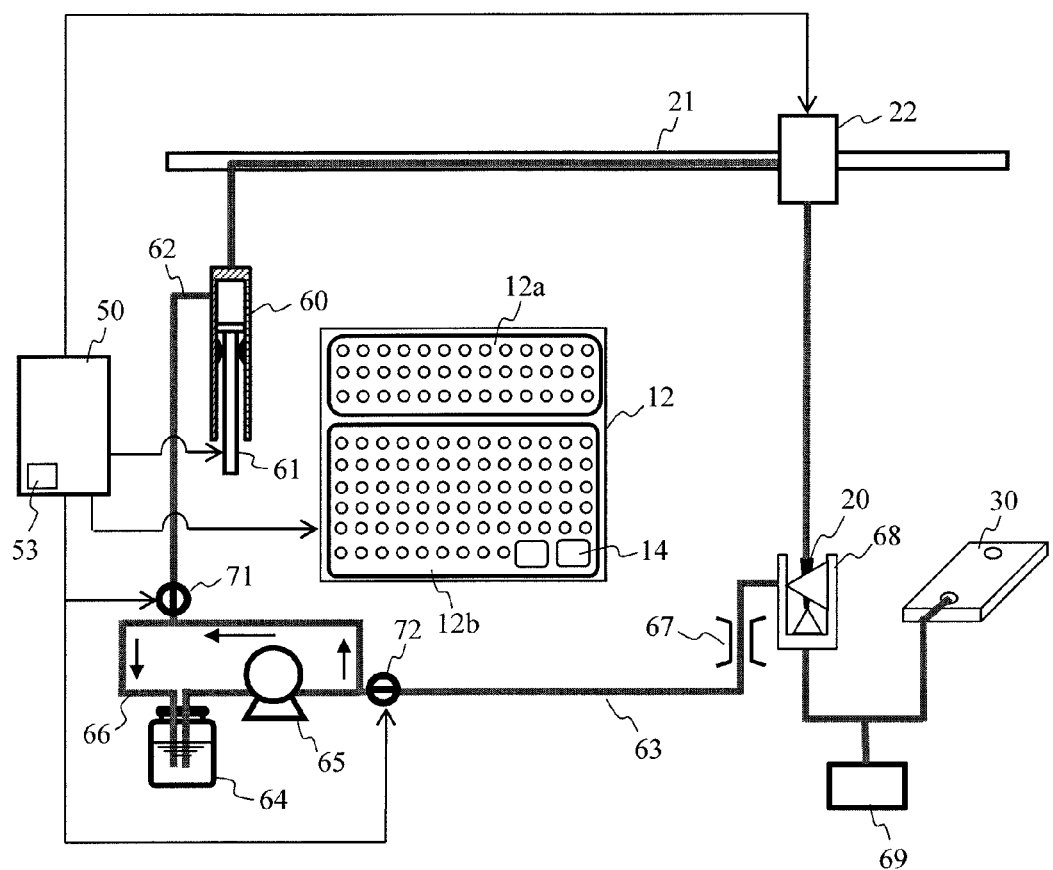
FIG. 5 is a schematic cross-sectional view showing how to clean a sampling nozzle in a cleaning tank.

Next, the control/operation unit 50 controls the second electromagnetic valve 72 to be open, the second electromagnetic valve 72 being connected to the cleaning liquid circulation passage 66 (S13). Then, cleaning liquid that is sent under pressure from the pump 65 flows through the second electromagnetic valve 72 and the second passage 63 and is sprayed from the inner wall of the cleaning tank 68, thus cleaning the outside of the sampling nozzle 20 located in the cleaning tank 68. In this way, as shown in FIG. 5, the inside and the outside of the sampling nozzle 20 are cleaned. After finishing the cleaning, the control/operation unit 50 closes the first electromagnetic valve 71 and the second electromagnetic valve 72 (S14).

Instead of firstly opening the first electromagnetic valve 71 and then opening the second electromagnetic valve 72, the first electromagnetic valve 71 and the second electromagnetic valve 72 may be opened at the same time. In this case, the inside and the outside of the sampling nozzle will be cleaned at the same time. The ordering of cleaning may be the outside of the nozzle first and then the inside of the nozzle.

In any case, at the time when the cleaning of the inside of the sampling nozzle is finished and the first electromagnetic valve 71 is closed, the first passage 62 connected to the cleaning liquid circulation passage 66, the microsyringe 60 and the tip end of the sampling nozzle 20 are filled with the cleaning liquid.

The cleaning method of the present embodiment enables supplying of a large quantity of cleaning liquid to the inside or the outside of the sampling nozzle or both of the inside and the outside of the sampling nozzle in a short time, thus shortening the cleaning duration and improving throughput of analysis.

(2) Flow Cell Cleaning

Figure 7:
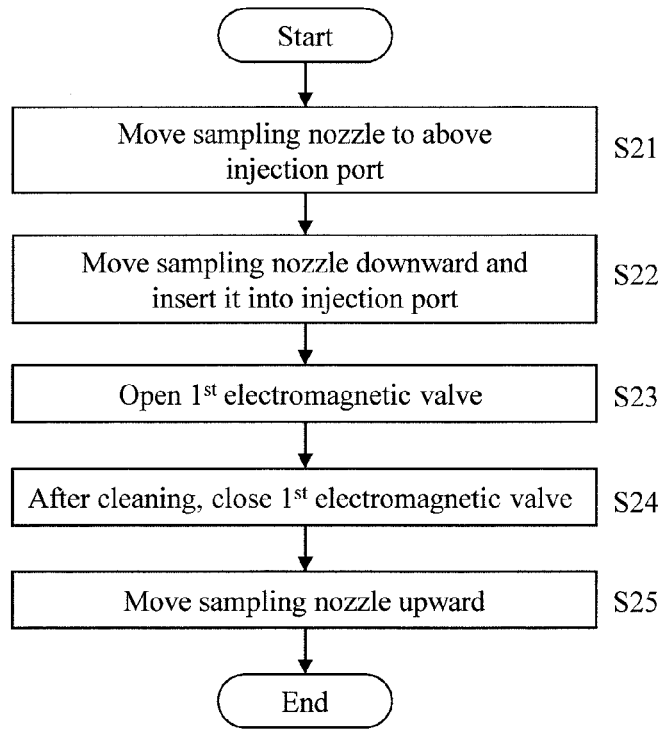
FIG. 7 is a flowchart showing control procedure to clean the inside of a flow cell.

Next, the inside of the flow cell 30 is cleaned. FIG. 5 is a schematic cross-sectional view showing the cleaning of the sampling nozzle in the cleaning tank. FIG. 7 is a flowchart showing the procedure of control by the control/operation unit 50 at that time.

The control/operation unit 50 controls the nozzle driving mechanism to move the sampling nozzle 20 to a position above the injection port 32 of the flow cell 30 (S21). Next, the sampling nozzle is moved downward, and as shown in FIG. 4, the tip end of the nozzle is inserted into the injection port (S22).

At this time, the rigidity of the arm 24, to which the rear end of the sampling nozzle 20 is fixed, is set so that the tip end of the nozzle can be inserted to follow the tapering of the injection port for complete sealing in spite of an error of about 1 to 2 mm between the position of the injection port of the flow cell and the tip end position of the sampling nozzle. Although the sampling nozzle is made of metal, it is too thin to have large rigidity. If the rigidity of the arm 24 is set large as in a typical automatic analyzer, a positioning error of the tip end of the sampling nozzle relative to the injection port of the flow cell will be absorbed by bending of the sampling nozzle. Then, the relationship of the tip end of the sampling nozzle 20 relative to the rotating shaft 23 will be different from the original setting, thus failing in precise positioning of the nozzle tip end and so failing to suck a desired reagent and to inject a reagent to the flow cell. Then, instead of absorbing a positioning error, if any, of the tip end of the sampling nozzle relative to the injection port by the bending of the sampling nozzle only, the rigidity of the arm 24 is set lower so that the flexibility of the arm 24 can absorb such an error as much as possible. In this way, rigidity of the arm is set lower so that the arm itself can bend when the sampling nozzle is inserted into the tapered injection port of the flow cell, whereby the arm as well as the sampling nozzle bend, which can absorb the positioning error of the sampling nozzle by the nozzle driving mechanism.

Next the control/operation unit opens the first electromagnetic valve 71 (S23). At this time, the plunger 61 of the microsyringe 60 may be fixed or may move. Then, cleaning liquid that is sent under pressure from the pump 65 enters the microsyringe 60 via the first electromagnetic valve 71 and the first passage 62 and then flows from the tip end of the sampling nozzle 20, passes through the injection port 32 and flows into the passage 34 of the flow cell 30, thus cleaning the flow cell. The cleaning liquid after cleaning the passage of the flow cell is stored in the waste liquid tank 69. After finishing the cleaning of the flow cell while letting the first electromagnetic valve 71 open for predetermined duration, then the control/operation unit 50 closes the first electromagnetic valve 71 (S24). Thereafter the control/operation unit 50 controls the nozzle driving mechanism to move the sampling nozzle 20 upward and away from the injection port 32 (S25). At this time, the control/operation unit 50 does not instruct the nozzle driving mechanism to move the sampling nozzle upward immediately after closing the first electromagnetic valve 71, but waits for predetermined duration until the pressure of cleaning liquid in the flow cell becomes stable, and then instructs to move the sampling nozzle upward. This will be described in more detail relating to the injection of a reagent to the flow cell.

(3) Suction of Reagent from Reagent Container

Figure 8:
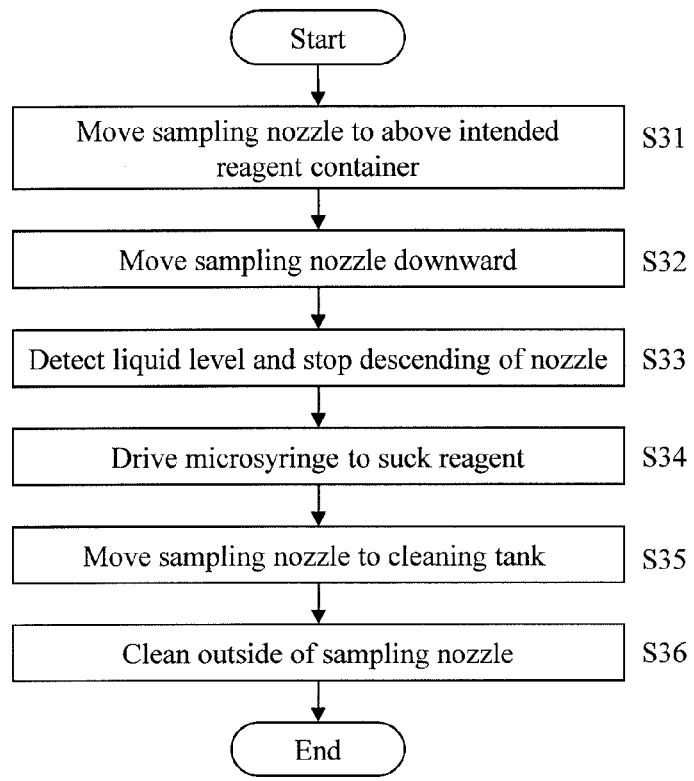
FIG. 8 is a flowchart showing procedure to suck a reagent from a reagent container.

Referring to the flowchart of FIG. 8, the following describes the procedure to suck a reagent from a reagent container 11 at a predetermined position in the reagent rack 12 by the sampling nozzle 20.

The control/operation unit 50 determines types of reagents to be sucked and their suction amounts in accordance with the procedure programed beforehand, and then refers to information on a correspondence relationship between the positions of reagent containers and types of reagents stored in the memory, thus determining the movement position of the sampling nozzle. Next the control/operation unit 50 controls the nozzle driving mechanism to move the sampling nozzle 20 at a position above the reagent container containing a target reagent (S31). Subsequently the sampling nozzle is moved downward so that the tip end of the nozzle comes into the reagent container (S32). At this time, the liquid level of the reagent in the reagent container is detected using the liquid level detection function of the liquid level detection unit 53. When detecting the liquid level of the reagent, then the sampling nozzle is further moved downward by a certain distance therefrom and descending of the sampling nozzle is stopped at the position where the tip end of the nozzle is inserted into the reagent solution by a predetermined depth (S33). Next, the control/operation unit 50 drives the plunger 61 of the microsyringe 60 by a predetermined amount to the suction side so as to suck the determined amount of reagent to be held ahead of a part the sampling nozzle 20 filled with the cleaning liquid (S34).

Next the control/operation unit 50 controls the nozzle driving mechanism to drive the sampling nozzle upward to let the tip end of the nozzle come out of the reagent container, and to move the sampling nozzle to the cleaning tank 68 (S35). Thereafter the control/operation unit 50 opens the second electromagnetic valve 72. Then, cleaning liquid is sprayed from the inner wall of the cleaning tank 68, thus rinsing off the reagent attached to the outside of the sampling nozzle 20 (S36). The reagent sucked in the sampling nozzle is not rinsed but is held in the nozzle as it is. When the cleaning of the outside of the sampling nozzle is finished, the control/operation unit 50 closes the second electromagnetic valve 72 and controls the nozzle driving mechanism to move the sampling nozzle 20 upward.

Since the tip end of the sampling nozzle 20 is inserted into the reagent by a minimum required depth by the liquid level detection function, the amount of reagent attached to the outside of the sampling nozzle 20 and to be rinsed off in the cleaning tank 68 can be always minimized. As another advantage of the liquid level detection of reagent, the remaining amount of reagent can be understood from the shape of a reagent container and the liquid level height. This enables calculation of the number of remaining bases that can be analyzed and allows a user to know the timing to replace the reagent.

(4) Injection of Reagent to Flow Cell

Figure 9:
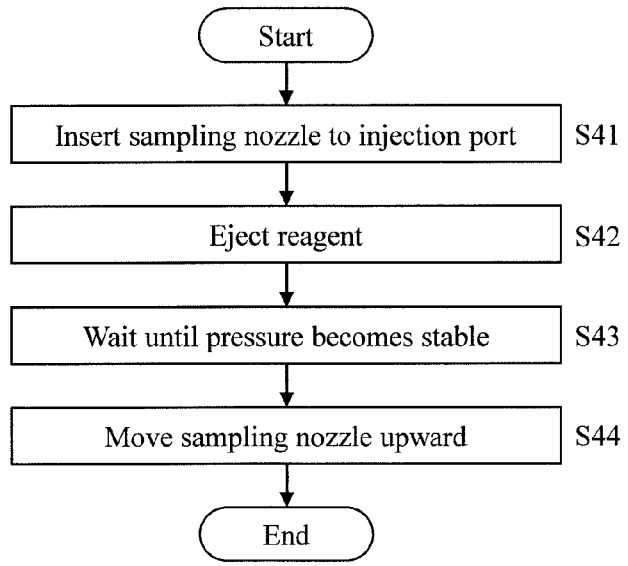
FIG. 9 is a flowchart showing exemplary procedure to inject a reagent into a flow cell.

Referring to the flowchart of FIG. 9, the following describes the procedure to inject a reagent sucked and held at the tip end of the sampling nozzle 20 into the flow cell 30.

Firstly, the control/operation unit 50 controls the nozzle driving mechanism to move the sampling nozzle 20 to a position above an injection port 32 of the flow cell 30. Next, the sampling nozzle 20 is moved downward, and as shown in FIG. 4, the tip end of the nozzle is inserted into the injection port 32 (S41). A positioning error of the tip end of the sampling nozzle 20 relative to the injection port 32, if any, can be absorbed by the flexibility of the arm 24, to which the rear end of the sampling nozzle 20 is fixed, and so the tip end of the nozzle can be inserted into the injection port 32 to follow the tapering of the injection port 32 without damaging the sampling nozzle. Subsequently the control/operation unit 50 drives the plunger 61 of the microsyringe 60 to the ejection direction to inject the reagent sucked ahead of a part of the sampling nozzle 20 filled with the cleaning liquid into the flow cell 30 via the injection port 32 (S42). After the driving of the plunger 61 is finished, the control/operation unit 50 waits until the pressure in the flow cell 30 becomes stable (S43), and then controls the nozzle driving mechanism to draw the sampling nozzle upward (S44).

Figure 10:
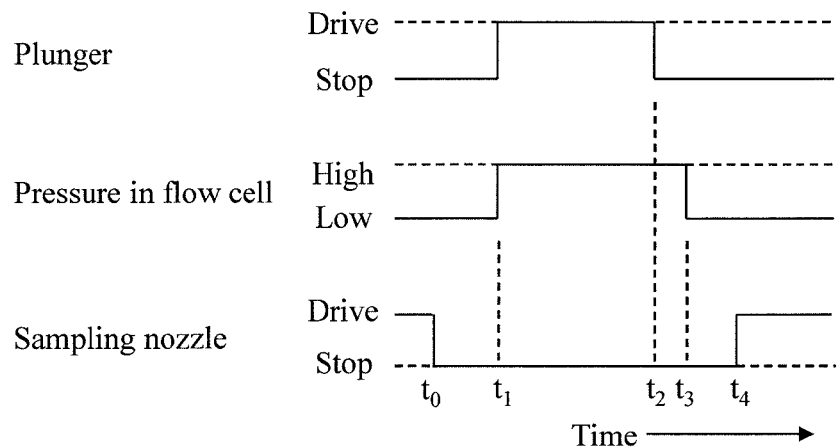
FIG. 10 schematically shows a relationship among the timings of insertion/removal of a sampling nozzle to/from an injection port, the timing of driving of a plunger of a microsyringe and a change in pressure in a flow cell.

FIG. 10 schematically shows a relationship among the timings of insertion/removal of a sampling nozzle to/from an injection port, the timing of driving of the plunger of the microsyringe and a change in pressure in the flow cell. The horizontal axis represents time. FIG. 10 shows that the sampling nozzle 20 is inserted into an injection port 32 of the flow cell at time $t_0$ and is drawn upward from the injection port 32 at time $t_4$. The plunger 61 of the microsyringe 60 is driven for reagent ejection from time $t_1$ to $t_2$.

A reagent is injected under pressure into a passage of the flow cell having small conductance by driving the plunger 61 of the microsyringe 60. Thus the pressure in the flow cell 30 is high immediately after stopping of the driving (time $t_2$) of the plunger 61. As such, if the sampling nozzle 20 is separated from the injection port 32 soon, then the reagent may flow backward and spill out from the injection port 32. In the present embodiment, after waiting for duration until the pressure in the flow cell 30 becomes stable after the ending time $t_2$ of the reagent injection operation, then the sampling nozzle 20 is separated from the injection port 32 and is drawn upward. That is, time $t_4$ when the sampling nozzle 20 is to be drawn upward from the injection port 32 is set as $t_4 > t_3$. Such waiting time ($t_3 - t_2$) until the pressure in the flow cell becomes stable depends on the viscosity of a reagent injected, injection speed, passage resistance of the flow cell and the like, and typically may be about 0.5 second to 1 second.

After injection of a reagent into the flow cell, the control/operation unit 50 controls the nozzle driving mechanism to move the sampling nozzle 20 to the cleaning tank 68. Then, the inside and the outside of the sampling nozzle are cleaned by the procedure shown in "(1) Sampling nozzle cleaning" and the device stands by for the next operation.

According to the procedure to suck and inject a reagent shown in the present embodiment, the amount obtained by adding the volume corresponding to dead spaces generated at parts of the injection ports 32 of the flow cell to the capacity of the flow cell is enough for the amount of the reagent to be injected from the sampling nozzle to the flow cell. The estimated volume for such dead spaces is 5 µL or less. This means that the amount of a reagent to be injected to the flow cell 30, i.e., the necessary amount of a reagent to be sucked to the sampling nozzle 20 from a reagent container 11 is the amount corresponding to at least the volume of the sampling nozzle 20, and the amount obtained by adding 5 µL to 10 µL at most to the volume of the flow cell suffices. In this way, the present embodiment sucks a small amount of reagent from a reagent container for injection to the flow cell, and rinses off a small amount of reagent attached to the outside of the sampling nozzle 20. That is, the amount of a reagent used is small, and so the wasted amount of reagent also is small. Thus the present embodiment enables effective usage of an expensive reagent.

The present embodiment further achieves sucking of a reagent and sending the same to the flow cell by a sampling nozzle, and so can shorten the solution sending time compared with a method using a tube and a switching valve. Further carryover of a reagent hardly occurs, and so a purer reagent can be supplied to the flow cell, whereby the limit in number of bases for sequencing can be increased.

(5) Detection

Figure 11:
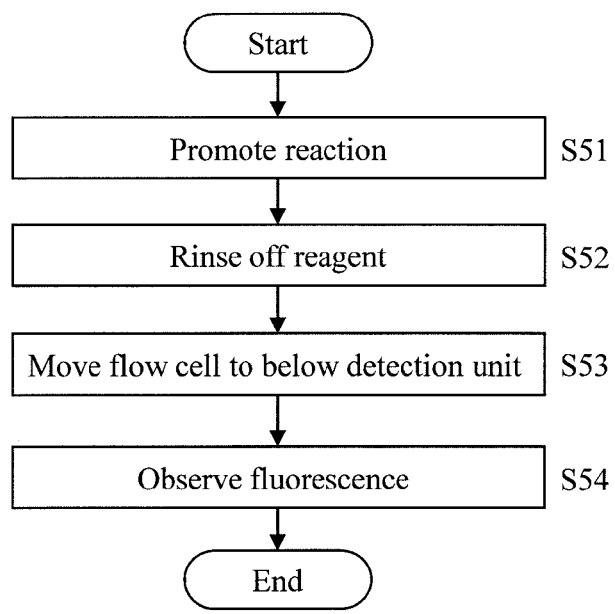
FIG. 11 is a flowchart showing procedure of detection.

Referring to the flowchart of FIG. 11, the following describes procedure for detection.

After injecting a reagent into the flow cell, the temperature of the flow cell 30 is controlled at a temperature suitable for a reaction (S51). Such a temperature control for the nucleic acid sample immobilized in the passage of the flow cell and the reagent initiates the reaction. After the reaction ends, the control/operation unit 50 performs the processing described above in "(2) flow cell cleaning" or the processing described in "(3) suction of reagent from reagent container and (4) injection of reagent to flow cell" for the cleaning liquid (reagent) placed at the reagent rack 12, thus cleaning the inside of the cell to rinse off an unreacted reagent (S52). Next the control/operation unit 50 drives and controls the flow cell stage 31 to move the flow cell 30 to a position below the detection unit 40 (S53). Next the control/operation unit 50 controls the detection unit 40 to apply excitation light and detect fluorescence emitted from the nucleic acid sample in the flow cell 30 (S54).

(6) Mixture of Reagents at Premixing Cell

Figure 12:
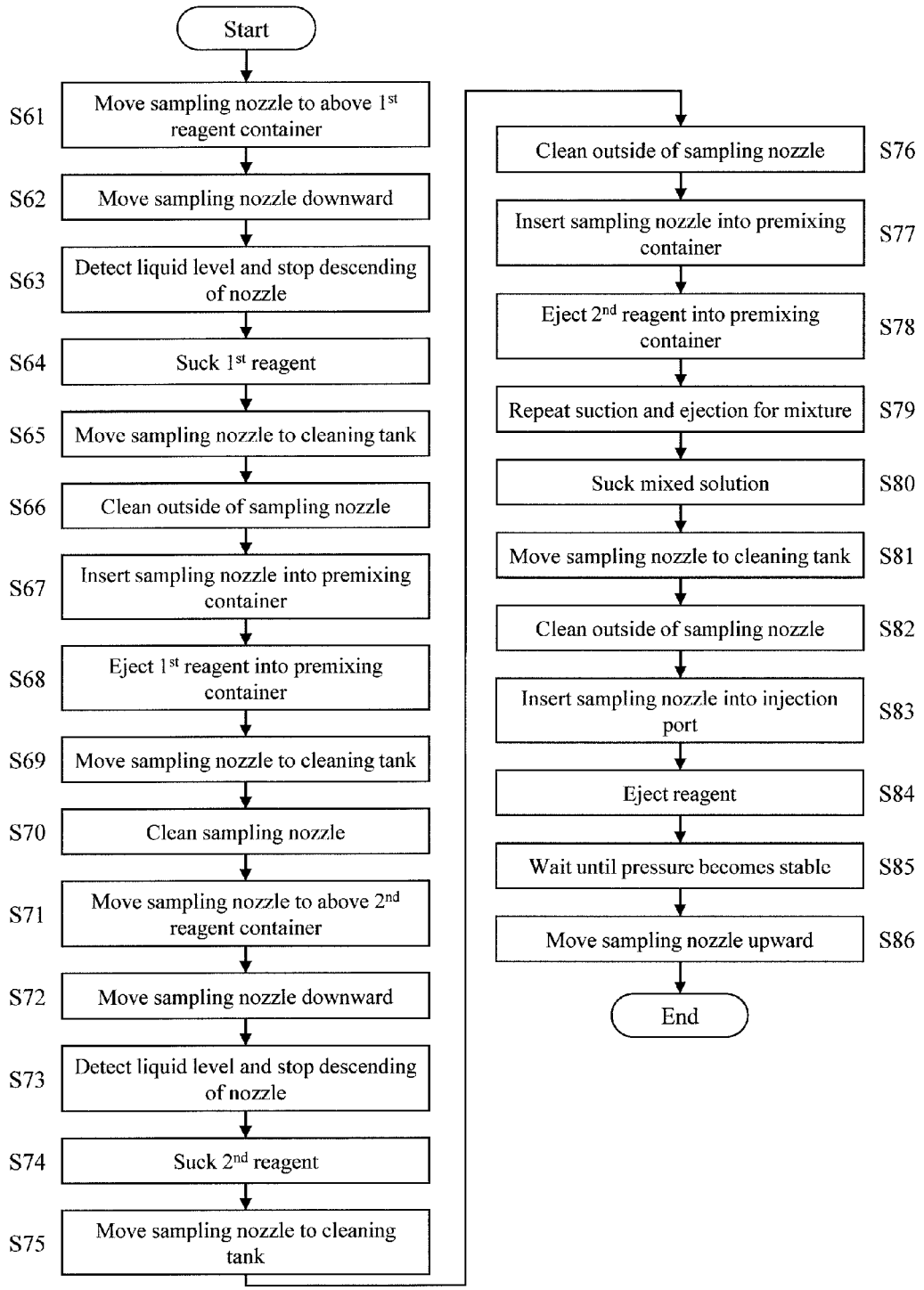
FIG. 12 is a flowchart showing procedure to mix two types of reagents and then inject the mixture into a flow cell.

Referring to the flowchart of FIG. 12, the following describes procedure to, immediately before the use, mix two types of reagents (a first reagent and a second reagent), and then inject the mixture to a flow cell.

Firstly the control/operation unit 50 controls the nozzle driving mechanism to move the sampling nozzle 20 to above a reagent container containing the first reagent (S61). Next the control/operation unit 50 moves the sampling nozzle 20 downward so that the tip end of the nozzle is inserted into the reagent container of the first reagent (S62). At this time, the liquid level of the reagent is detected by the liquid level detection function. When detecting the liquid level, the sampling nozzle 20 is further moved downward therefrom by a certain distance, and descending of the sampling nozzle 20 is stopped at the position where the tip end of the nozzle is inserted into the reagent solution by a predetermined depth (S63). Next the control/operation unit 50 drives the plunger 61 of the microsyringe 60 by a predetermined amount to the suction side so as to suck the determined amount of the first reagent to be held ahead of a part of the sampling nozzle 20 filled with the cleaning liquid (S64).

Next, the control/operation unit 50 controls the nozzle driving mechanism to drive the sampling nozzle upward to let the tip end of the nozzle come out of the reagent container of the first reagent, and further to move the sampling nozzle 20 to the cleaning tank 68 (S65). Thereafter the control/operation unit 50 opens the second electromagnetic valve 72. Then, cleaning liquid is sprayed from the inner wall of the cleaning tank, thus rinsing off the first reagent attached to the outside of the sampling nozzle (S66). Since the tip end of the nozzle is inserted into the first reagent by a minimum required depth by the liquid level detection function, the amount of the first reagent attached to the outside of the sampling nozzle and to be rinsed off is very small. After the cleaning of the outside of the sampling nozzle is finished, the control/operation unit 50 closes the second electromagnetic valve 72.

Next the control/operation unit 50 controls the nozzle driving mechanism to move the sampling nozzle 20 to above the premixing container 14 and move it downward so that the sampling nozzle is inserted into the premixing container (S67). Subsequently the control/operation unit 50 drives the plunger 61 of the microsyringe 60 to the ejection direction to eject the first reagent sucked ahead of a part of the sampling nozzle 20 filled with the cleaning liquid into the premixing container 14 (S68).

Next the control/operation unit 50 controls the nozzle driving mechanism to move the sampling nozzle 20 to the cleaning tank 68 (S69). Then, the inside and the outside of the sampling nozzle 20 are cleaned by the procedure described in "(1) Sampling nozzle cleaning" (S70).

Next the control/operation unit 50 controls the nozzle driving mechanism to move the sampling nozzle 20 to above a reagent container containing the second reagent (S71). Next the control/operation unit 50 moves the sampling nozzle 20 downward so that the tip end of the nozzle is inserted into the reagent container of the second reagent (S72). At this time, the liquid level of the reagent is detected by the liquid level detection function. When detecting the liquid level, the sampling nozzle 20 is further moved downward therefrom by a certain distance, and descending of the sampling nozzle is stopped at the position where the tip end of the nozzle is inserted into the reagent solution by a predetermined depth (S73). Next the control/operation unit 50 drives the plunger 61 of the microsyringe 60 by a predetermined amount to the suction side so as to suck the determined amount of the second reagent to be held ahead of a part of the sampling nozzle 20 filled with the cleaning liquid (S74).

Next, the control/operation unit 50 controls the nozzle driving mechanism to drive the sampling nozzle upward to move the sampling nozzle 20 to the cleaning tank 68 (S75). Then the control/operation unit 50 opens the second electromagnetic valve 72 connected to the cleaning liquid circulation passage 66. Then, cleaning liquid that is sent under pressure from the pump 65 is sprayed from the inner wall of the cleaning tank 68 through the second electromagnetic valve 72 and the second passage 63, thus cleaning the outside of the sampling nozzle 20 placed in the cleaning tank 68 (S76). After finishing the cleaning, the control/operation unit closes the second electromagnetic valve.

Next the control/operation unit 50 controls the nozzle driving mechanism to move the sampling nozzle 20 to above the premixing container 14 and move it downward so that the sampling nozzle is inserted into the premixing container 14 (S77). Subsequently the control/operation unit 50 drives the plunger 61 of the microsyringe 60 to the ejection direction to eject the second reagent sucked ahead of a part of the sampling nozzle 20 filled with the cleaning liquid into the premixing container 14 (S78).

Next the control/operation unit 50 inserts the sampling nozzle 20 into the mixture solution of the first reagent and the second reagent so as not to let the sampling nozzle 20 collide with the bottom of the premixing container 14. Then the control/operation unit 50 drives the plunger 61 of the microsyringe 60 alternately to the suction side and to the ejection side several times, thus repeating the suction of the mixture solution of the first reagent and the second reagent to the sampling nozzle and the ejection of the same to the premixing container 14, thereby sufficiently mixing the first reagent and the second reagent (S79). This process is performed so as to avoid excessive driving of the plunger 61 to the ejection side and so ejection of the cleaning liquid from the sampling nozzle 20 to the premixing container 14.

When the mixture of the first reagent and the second reagent in the premixing container 14 is finished, the control/operation unit 50 drives the plunger 61 of the microsyringe 60 to the suction side to suck the mixture solution at the tip end of the sampling nozzle 20 (S80).

Subsequently the control/operation unit 50 controls the nozzle driving mechanism to move the sampling nozzle 20 to the cleaning tank 68 (S81). Then the control/operation unit 50 controls the second electromagnetic valve 72 to be open, the second electromagnetic valve 72 being connected to the cleaning liquid circulation passage 66. Then, cleaning liquid that is sent under pressure from the pump 65 is sprayed from the inner wall of the cleaning tank 68 through the second electromagnetic valve 72 and the second passage 63, thus cleaning the outside of the sampling nozzle 20 placed in the cleaning tank 68 (S82). After finishing the cleaning, the control/operation unit 50 closes the second electromagnetic valve 72.

Next the control/operation unit 50 injects the mixture reagent of the first reagent and the second reagent to the flow cell 30 by the procedure described above in "(4) injection of reagent to flow cell" (S83 to S86).

After injecting the mixture reagent to the flow cell, the inside and the outside of the sampling nozzle 20 are cleaned by the procedure described in "(1) Sampling nozzle cleaning" (S70).

Subsequently, if needed, the premixing container 14 is cleaned. For the cleaning of the premixing container 14, the control/operation unit 50 moves the sampling nozzle 20 to the premixing container 14 after use, and opens the first electromagnetic valve 71 so as to inject a sufficient amount of cleaning liquid to the premixing container 14. Then the control/operation unit 50 drives the plunger 61 of the microsyringe 60 alternately to the suction side and to the ejection side several times, thus rising off the reagent attached to the inner wall of the premixing container 14 by the cleaning liquid. After finishing the cleaning of the inner wall of the premixing container, the control/operation unit 50 drives the plunger 61 of the microsyringe 60 to the suction side to suck the cleaning liquid in the premixing container 14 to the sampling nozzle 20. Subsequently the control/operation unit 50 moves the sampling nozzle 20 to the cleaning tank 68 and opens the first electromagnetic valve 71 and the second electromagnetic valve 72, thus discharging the sucked cleaning liquid while cleaning the inside and the outside of the sampling nozzle 20.

The above describes the example of mixing two types of reagents, and the procedure to mix three or more types of reagents and inject the thus prepared mixture reagent to the flow cell also may be performed based on the similar principle as the above. Alternatively, a plurality of types of reagents may be sucked continuously and then may be ejected collectively to the premixing container 14.

According to the solution sending system of the present embodiment based on the operation of suction and ejection at the tip end of the sampling nozzle that is filled with the cleaning liquid, a reagent injected to the flow cell and undergone a reaction may be sucked from the injection port by the sampling nozzle and may be reused for another reaction. The amount of a reagent injected into the flow cell and is actually used in the reaction and is consumed is only 1% of the total amount of the reagent. This means that the reagent undergone a reaction and collected from the flow cell has density and purity that can be sufficiently reused.

FIG. 13 is a flowchart showing the procedure to collect a reagent from the flow cell. A reagent is collected when the reaction is finished in the flow cell and prior to the timing when the reagent is rinsed off by cleaning liquid.

The control/operation unit 50 controls the nozzle driving mechanism to insert the sampling nozzle 20 to an injection port 32 of the flow cell 30 where the reaction ends (S91). Next the control/operation unit 50 drives the plunger 61 of the microsyringe 60 to the suction side to suck the reagent in the flow cell 30 (S92). Next the control/operation unit 50 controls the nozzle driving mechanism to move the sampling nozzle 20 to a container for collected reagent that is prepared at the reagent rack 12 (S93) and to eject the sucked reagent to the container for collection (S94). It will be understood that the container for collected reagent is prepared separately for each type of reagent. After finishing the collection of the reagent, the control/operation unit 50 controls the nozzle driving mechanism to move the sampling nozzle 20 to the cleaning tank 68 to clean the inside and the outside of the sampling nozzle 20, and stands by for the next operation. The reagent collected in the container for reagent collection may be used similarly to the reagent in a normal reagent container. According to the present embodiment, a reagent can be used more effectively, which contributes to a decrease in cost for analysis.

FIG. 14 is a schematic cross-sectional view showing another embodiment of the reagent rack. The reagent rack of the present embodiment has a cover 15 that is movable in a sliding manner at the top face thereof. A reagent put in a container opening at the top will evaporate or the oxidation of the reagent progresses. To avoid this, the cover 15 is provided on the reagent rack 12, the cover having a plurality of openings 16 at positions corresponding to the positions of the reagent containers so as to allow the tip end of the sampling nozzle to pass therethrough. The cover 15 can move in a sliding manner in a uniaxial direction by a motor 17 that is driven by an instruction from the control/operation unit 50. The cover 15 is positioned by the motor 17 so that the position of the opening for a reagent container that is not used is shifted to cover the upper part of the container and the position of the opening for a reagent container that is used agrees with the position of the reagent container so as to allow the sampling nozzle access thereto. The present embodiment mitigates problems such as evaporation and oxidation of a reagent.

The above-described embodiment shows that a reagent is sucked at the leading end of the cleaning liquid charged at the sampling nozzle so as to come into contact with the cleaning liquid at their interfaces. Alternatively, about 5 µL of air may be sucked prior to the suction of a reagent to form an air layer between the cleaning liquid and the reagent so as to suck and hold the reagent at the leading end of the sampling nozzle while keeping away from the cleaning liquid. In this case, in order to avoid introduction of air into the flow cell when ejecting the reagent to the flow cell, a little bit extra amount of the reagent may be sucked beforehand and the reagent may be ejected while leaving a small amount of the reagent in the sampling nozzle when injecting the reagent to the flow cell.

The solution sending system of the above-described embodiment includes the cleaning liquid circulation passage 66 provided with the pump 65, where the cleaning liquid is supplied from the cleaning liquid circulation passage 66 to the first passage 62 or the second passage 63 via the electromagnetic valves 71 or 72. However, the cleaning liquid circulation passage is not always necessary.

Figure 15:
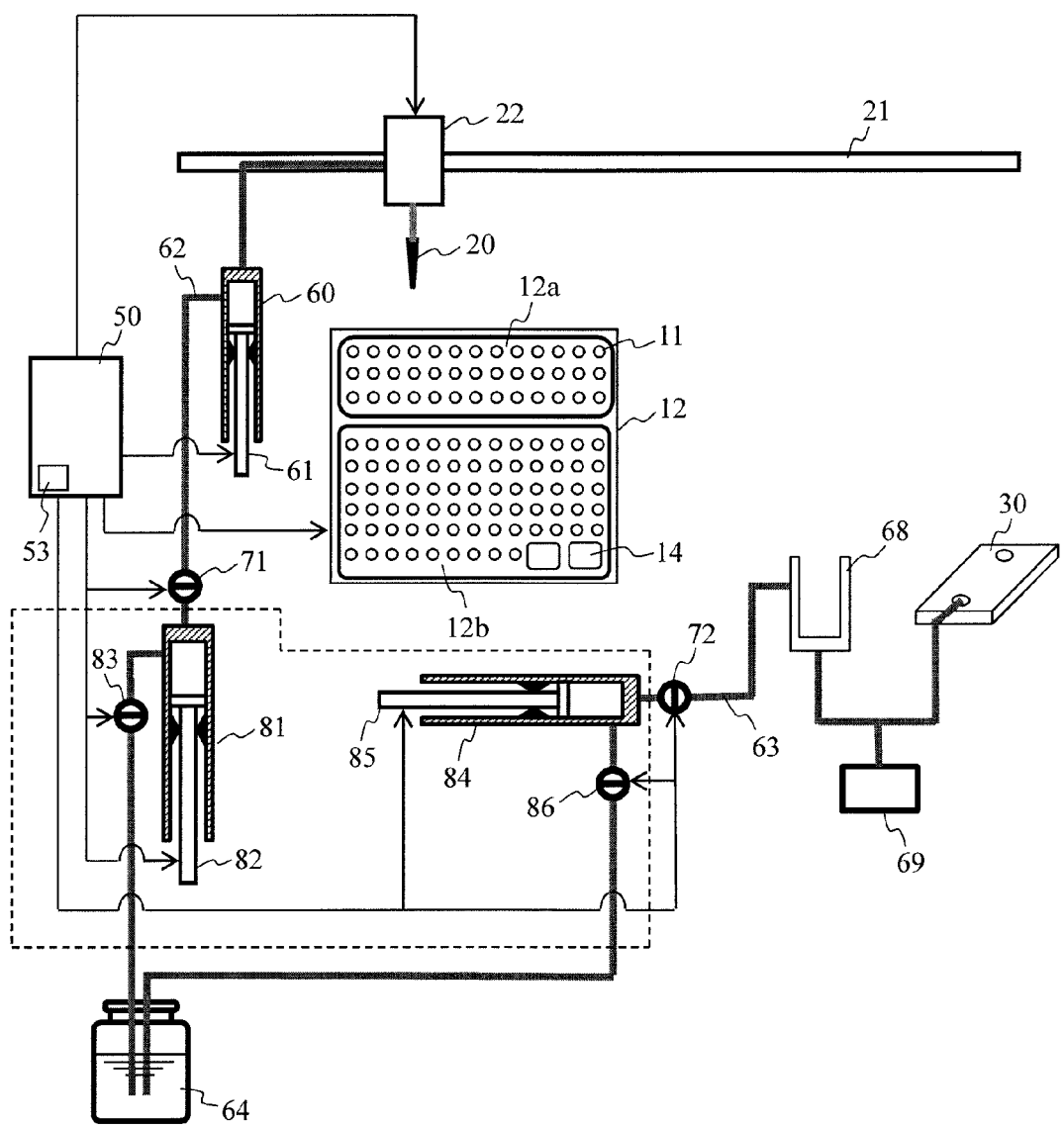
FIG. 15 is a schematic view showing another exemplary solution sending system.

FIG. 15 schematically shows an exemplary solution sending system without a cleaning liquid circulation passage. The solution sending system of the present embodiment is different from the solution sending system of the embodiment of FIG. 2 in elements within the dotted line. The solution sending system of the present embodiment includes a first cleaning liquid syringe 81 to send cleaning liquid that is located on the upstream side of the first electromagnetic valve 71 disposed at the first passage 62 communicating with the sampling nozzle 20 and a third electromagnetic valve 83 between the first cleaning liquid syringe 81 and the cleaning liquid tank 64. This solution sending system further includes a second cleaning liquid syringe 84 to send cleaning liquid that is located on the upstream side of the second electromagnetic valve 72 disposed at the second passage 63 opening at the inner wall of the cleaning tank 68 and a fourth electromagnetic valve 86 between the second cleaning liquid syringe 84 and the cleaning liquid tank 64. The control/operation unit 50 controls, in addition to the first electromagnetic valve 71 and the second electromagnetic valve 72, the third electromagnetic valve 83, a plunger 82 of the first cleaning liquid syringe 81, the fourth electromagnetic valve 86 and a plunger 85 of the second cleaning liquid syringe 84.

Cleaning liquid is ejected from the tip end of the sampling nozzle in the following procedure. The control/operation unit 50 drives, in the state of closing the first electromagnetic valve 71 and opening the third electromagnetic valve 83, the plunger 82 of the first cleaning liquid syringe 81 to the suction side to suck cleaning liquid to the first cleaning liquid syringe 81 from the cleaning liquid tank 64. After finishing the sucking of the cleaning liquid, the control/operation unit 50 closes the third electromagnetic valve. Such procedure may be executed at spare time when the sampling nozzle does not eject the cleaning liquid for preparation in advance. Then, at the timing when the ejection of cleaning liquid is requested, the control/operation unit 50 opens the first electromagnetic valve 71 and drives the plunger 82 to the ejection direction. Thereby the cleaning liquid is ejected from the tip end of the sampling nozzle 20. The plunger 61 of the microsyringe 60 is kept fixed. Herein, driving of the plunger 61 of the microsyringe 60 to the ejection side concurrently with the driving of the plunger 82 can increase the flowing speed of the cleaning liquid that is ejected from the sampling nozzle.

The cleaning liquid is sprayed from the inner wall of the cleaning tank 68 in the cleaning tank 68 in the following procedure. The control/operation unit 50 drives, in the state of closing the second electromagnetic valve 72 and opening the fourth electromagnetic valve 86, the plunger 85 of the second cleaning liquid syringe 84 to the suction side to suck cleaning liquid to the second cleaning liquid syringe 84 from the cleaning liquid tank 64. After finishing the sucking of the cleaning liquid, the control/operation unit 50 closes the fourth electromagnetic valve. Such procedure may be executed at spare time when the cleaning liquid is not sprayed in the cleaning tank 68 for preparation in advance. Then, at the timing when the ejection of cleaning liquid to the cleaning tank 68 is requested, the control/operation unit 50 opens the second electromagnetic valve 72 and drives the plunger 85 to the ejection direction. Thereby the cleaning liquid is sprayed from the inner wall of the cleaning tank 68.

The operation to suck/eject a reagent using the microsyringe 60 is the same as in the solution sending system shown in FIG. 2.

In the actual device, the positional error between the sampling nozzle 20 and the injection port 32 has to be ±1 mm or less, preferably ±0.5 mm or less. The device may be configured so that errors of the initial setting values do not change as long as nothing comes into contact with the sampling nozzle 20, for example. However, if the sampling nozzle 20 is replaced or is touched or bent erroneously, the rotating diameter of the sampling nozzle 20 relative to the rotating shaft 23 may change actually. For instance, when the rotating diameter is 100 mm and the sampling nozzle 20 bends outward by 1 mm, the rotating diameter will be 101 mm, and when the sampling nozzle 20 bends inward by 1 mm, the rotating diameter will be 99 mm. In preparation for such a case, the position of the sampling nozzle 20 has to be calibrated. When the sampling nozzle 20 bending greatly descends, it will collide with the cover 15, for example. A jamming sensor not illustrated that detects the rising of the sampling nozzle 20 due to the collision may prevent breakage of the sampling nozzle 20 without calibrating the displacement. However, it will take time to move the sampling nozzle 20 and visually reposition the reagent container 11, the cleaning tank 68 and the injection port 32 performed every time when such displacement occurs, and such an operation also fails to make sure that the sampling nozzle 20 enters the injection port 32 because an error will change from person to person who performs repositioning. Thus a method for automatic calibration of the sampling nozzle 20 is required.

The following describes a method of providing positioning pins 18 at the reagent rack 12, the cover 15 to be placed on the reagent rack 12, the cleaning tank 68, the flow cell stage 31, the injection port 32 and the like, thus automatically positioning the sampling nozzle 20. Herein, the positions and the number of the positioning pins 18 are not limited those in the drawings. The positioning pins include a metal part corresponding to substantially the outer diameter of the sampling nozzle in size (e.g., 0.1 to 1 mm, which is not restrictive), and as shown in the enlarged view of a pin 18c surrounded with the dotted line in FIG. 14, it is coated with a non-conductive substance such as plastic. Conversely, a positioning part may be made of a non-conductive substance that does not perform liquid level detection, and a part other than that may be made of a conductive substrate for liquid level detection as in the opening 16. The structure of the positioning pins 18 is not limited to this. When the arm 24 descends until the tip end of the sampling nozzle 20 comes into contact with the conductive part of the positioning pins 18, then the liquid level detection function operates. This is based on the liquid level detection function operating when it comes into contact with the conductive part. On the other hand, when the arm 24 comes into contact with a non-conductive part, the liquid level detection function does not operate. Thus, the range where the liquid level detection function operates is determined by shifting the position of the arm 24 little by little, whereby the center of the positioning pins 18 can be found.

Simply determining the position of one positioning pin 18 does not mean accurate automatic calibration. This is because, for example, a larger device means a larger moving amount of the arm 24, and so an error will be piled up. Assume that the linear movement unit 22 moves 500 mm, for example. The linear movement unit 22 may be configured, for example, so that rotation of a motor not illustrated causes rotation of a gear not illustrated, and then a belt not illustrated attached to the gear rotates, whereby the linear movement unit 22 moves along the guide rail 21. When the gear has a diameter of $\phi 10$ mm, then the arm 24 will move the distance of 500 mm during 50 rotations of the gear, for example. Herein, the diameter of the gear has a mechanical error. If the diameter of the gear is larger by up to 50 μm, i.e., 10.05 mm, then the arm will move 502.5 mm including the extra of 2.5 mm during 50 rotations. As such, a plurality of positions may be found using the positioning pins, and the following parameters may be calculated, including the mechanical error, thus enabling calibration of the sampling nozzle 20.

Figure 16:
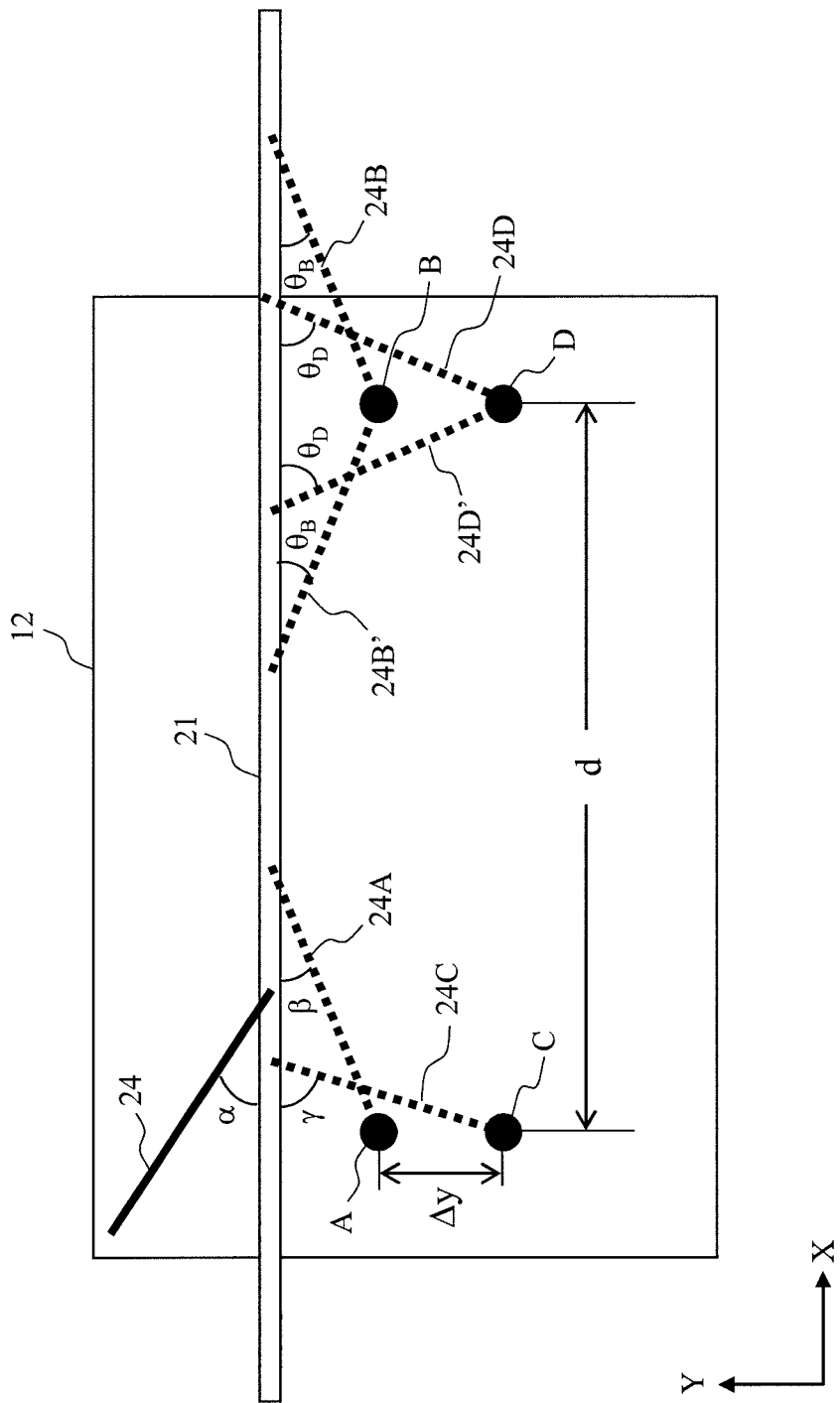
FIG. 16 explains a calibration method for movement of a sampling nozzle.

Referring to the example of FIG. 16 where four positioning pins 18 are disposed so as to configure a rectangle having known lengths at the reagent rack 12, the following describes a calibration method. The positions and the number of the positioning pins 18 are not limited to this. Since this calibration is not required for the case of a short distance between the sampling nozzle 20 and the injection port 32, for example, this is a new technical problem.

Assume herein that, as shown in FIG. 16, four positioning pins A to D are provided on the reagent rack 12. The position of each positioning pin is known, and the positioning pins A and B or the positioning pins C and D are away from each other by a known distance d, and the positioning pins A and C or the positioning pins B and D are away from each other by a known distance Δy. The line connecting the positioning pins A and B and the line connecting the positioning pins C and D are parallel to the guide rail 21. The position of the arm and the posture thereof around the rotating shaft depend on the movement along the guide rail 21 in the X-axis direction and the rotating angle around the rotating shaft. Assume herein that both of the movement of the arm in the X-axis direction and the rotation around the rotating shaft are implemented by pulse driving of a stepping motor. Then, the state of the arm 24A having the tip end thereof approach the center of the positioning pin A due to the liquid level detection function of the sampling nozzle is displayed as in $(X_A, T_A)$ using a set of a driving pulse number $X_A$ for the X-driving stepping motor and a driving pulse number $T_A$ for a stepping motor rotating the arm. Both of $X_A$ and $T_A$ are measurable amounts.

The calibration is performed by the following steps 1 to 5.

(1) Step 1

Dotted lines in FIG. 16 show the posture of the arm 24 when the arm 24 moves and the sampling nozzle 20 detects the positioning pins. The solid line of the arm 24 shows the initial angle of the rotating angle, indicating that the angle with reference to the guide rail 21 is α. β and γ also indicate angles with reference to the guide rail 21. The pulse number of X-movement of the arm from the state of the arm 24A where the sampling nozzle 20 detects the positioning pin A to the state of the art 24B where the sampling nozzle 20 detects the positioning pin B is divided by the distance, whereby the distance in the X direction where the arm 24 travels per one pulse that is a driving signal, i.e. a linear movement coefficient L is calculated. The state of the arm 24A is represented as $(X_A, T_A)$ and the state of the arm 24B is represented as $(X_B, T_B)$. Since $T_A = T_B$, the linear movement coefficient L can be found by the following expression:

$$L = d/(X_B - X_A) \tag{1}$$

Similar measurement is performed for the positioning pins C and D, and the average value may be calculated for the linear movement coefficient L. Although the guide rail 21 and the line connecting the positioning pins A and B are desirably parallel to each other, if the reagent rack 12 is not parallel to the guide rail 21, the arm has to be rotated for positioning from the position pins A to B. In this case, the sampling nozzle 20 is calibrated assuming that the positions of the reagent containers 11 are located at the θ-rotated (matrix calculation) positions of the reagent rack 12.

(2) Step 2

The arm is positioned with reference to the positioning pins B and D from two directions as in 24B and 24B' and 24D and 24D', whereby the arm rotating angle per one pulse as a driving signal, i.e., a rotary movement coefficient T and the rotating radius r of the arm 24 are calculated. The positioning of two points of the positioning pins B and D from two directions allows a simultaneous equation with two unknowns to be introduced for the calculation. Herein, the rotating radius r of the arm 24 refers to the distance to the tip end position of the sampling nozzle 20 with reference to the rotating shaft 23 exactly, which is called the rotating radius r of the arm for convenience sake.

For instance, when positioning is performed for the positioning pin B from two directions, the rotating radius r does not change, and so the triangle indicated with the dotted lines forms an isosceles triangle. The vertex angle thereof corresponds to the number of pulses of the arm required for the rotation. The length of the base can be calculated because the linear movement coefficient L that is the distance the linear movement unit 22 travels per one pulse in the X direction is known. Once the rotary movement coefficient T is known, the rotating radius r of the arm also can be calculated.

Based on the state $(X_B, T_B)$ of the arm 24B where the arm is positioned from right with reference to the positioning pin B and the state $(X_{B'}, T_{B'})$ of the arm 24B' where the arm is positioned from left with reference to the positioning pin B, the following expressions (2) and (3) hold. Herein, $\theta_{B'} = \theta_B$.

$$2\theta_B = (T_{B'} - T_B) \times T - \pi \tag{2}$$

$$L \times (X_{B'} - X_B) = 2r \cos \theta_B \tag{3}$$

Similar operation is performed for the positioning pin D. That is, based on the state $(X_D, T_D)$ of the arm 24D where the arm is positioned from right with reference to the positioning pin D and the state $(X_{D'}, T_{D'})$ of the arm 24D' where the arm is positioned from left with reference to the positioning pin D, the following expressions (4) and (5) are obtained.

$$2\theta_D = (T_{D'} - T_D) \times T - \pi \tag{4}$$

$$L \times (X_{D'} - X_D) = 2r \cos \theta_D \tag{5}$$

Substitution of $\theta_B$ in Expression (2) into (3) yields a relational expression of T and r, and similarly substitution of $\theta_D$ in Expression (4) into (5) yields another relational expression of T and r. Thereby the rotary movement coefficient T that is the arm rotating angle per one pulse and the rotating radius r of the arm 24 can be found.

Although T and r are found by positioning for two positioning pins in the above, similar operation may be performed for three or more positioning pins, and the average value of a plurality of values for T and r are found as the rotary movement coefficient T and the rotating radius of the arm.

(3) Step 3

Using the number of pulses required to rotate the arm for positioning from the positioning pin A (angle β) to the positioning pin C (angle γ), the known distance Δy and the rotating radius r of the arm found as above, angle β is calculated from the relationship of the following Expression (6):

$$r \sin \gamma - r \sin \beta = \Delta y \tag{6}$$

In Expression (6), the positioning from the state of angle β to angle γ can be performed by rotating the arm by the pulse number of $(T_C - T_A)$. That is, Expression (6) can be transformed into another expression including β only as an unknown, from which the angle β can be found. Once the angle β is known, the angle γ also can be found from Expression (6). The values of the angles are required because the rotation of the arm with the same number of pulses makes the sampling nozzle travel different distances in the Y direction depending on the initial position (angle α) of the arm, and so the values have to be found for the calibration.

(4) Step 4

Positions of the reagent containers 11, the premixing container 14, the opening 16, the injection ports 32 and the cleaning tank 68 with reference to the initial position of the arm are calculated, and the sampling nozzle 20 is positioned using the afore-mentioned calculated parameters.

(5) Step 5

For the Z direction, when the reagent rack 12 is made of metal, the height from the bottom face can be understood by the liquid level detection of the bottom face of the reagent rack excluding the reagent containers. For instance, calibration can be performed by setting the position obtained by subtracting the distance to the bottom face of the reagent containers from the position as the Z descending position. The gradient of the guide rail 21 with reference to the reagent rack 12 can be calculated.

The method for positioning described in Steps 1 to 4 is not limited to the method of the aforementioned embodiment that specifies the positions of the positioning pins by liquid level detection. Another method that specifies the positions of the pins (detecting using a sensor, for example), if any, enables positioning based on the similar methodology.

When the nozzle is replaced or bends, only the rotating radius of the arm 24 changes. Since the resolution per one pulse in X or θ does not change, simply positioning of the positioning pin 18*i* from two directions enables calibration. A log for the calibration may be saved, whereby errors of the calculated parameters can be verified.

When the control/operation unit 50 detects the calculated parameters beyond the estimated parameter range (that can be guessed from mechanical tolerance, a liquid level detection error and the like), the control/operation unit 50 may determine it as an abnormal state of the device, stop the operation of the device, specifically driving the sampling nozzle and announce the abnormality. Announcement of the abnormality may be performed by appropriate means such as warning sound, lightening of a lamp indicating abnormality or displaying abnormality on the display unit 52.

The control/operation unit 50 determines, as the abnormal state, the following cases.

(a) The calculated position of a reagent container (X, T) is beyond the movable range of X and T of the arm, which is so not accessible, or there is no solution for X and T.

(b) The calculated rotating radius r of the arm is smaller or is larger than a certain value. In this case, it is assumed that the sampling nozzle bends, and so the sampling nozzle may collide with a side wall of a reagent container.

(c) The gradient of the arm (X direction) with reference to the reagent rack, which is calculated from Z of the pins A and B by liquid level detection, is large. In this case, the sampling nozzle may collide with a side wall of the reagent container.

(d) The gradient of the rotating face of the tip end of the nozzle with reference to the reagent rack, which is calculated from Z for the case of accessing the positioning pins A and C from two directions by liquid level detection, is large. In this case, the sampling nozzle may collide with a side wall of the reagent container.

(e) The gradient of the face of the reagent rack, which is calculated from Z of the positioning pins A, B, C and D by liquid level detection, is large. In this case, the sampling nozzle may collide with a side wall of the reagent container.

Even without the occurrence of abnormality of the above (a) to (e) during inspections before shipment, the abnormality of the above (a) to (e) may occur when the sampling nozzle is replaced. This is because the sampling nozzle has tolerance such as in a bending angle, and so the rotating radius r of the arm will change every time when the sampling nozzle is replaced. Thus in addition to the inspections of the above (a) to (e) before shipment, the calculation may be performed by substitution of the maximum value and the minimum value of the rotating radius r of the sampling nozzle, whereby the risk of the abnormality of the above (a) to (e) can be avoided when the sampling nozzle is replaced. Available countermeasure therefor includes to replace the sampling nozzle and to readjust the installation positions and angles of the arm and the reagent rack.

The following describes, as one example, a method of determining base sequence by capturing molecules of a sample DNA fragment to be analyzed one by one, elongating each base and detecting molecules of the incorporated fluorescent label one by one. Specifically, the method includes the steps of: generating a DNA polymerase reaction using four types of dNTP derivatives, which are incorporated into a template of DNA as substrates of DNA polymerases, thus being capable of terminating a DNA strand elongation reaction by the presence of a protective group and which have detectable labels; then detecting the incorporated dNTP derivatives by fluorescence or the like and returning the incorporated dNTP derivatives to an extendible state, and these steps as one cycle are repeated, thus determining the base sequence of the sample DNA. At this time, various steps to send solution such as injecting a reagent to a flow cell and cleaning are performed by combining the steps of the present embodiment as described above in (1) to (6).

The sample DNA fragment is disposed at random in the flow cell by immobilizing biotinylated DNA to streptavidin beads and scattering the beads in the flow cell. The size of the beads is 2,000 nm or less, preferably 10 to 1,000 nm.

Various types of fluorescent substances may be used as a fluorescent label for the dNTP. For example, Bodipy-FL-510, R6G, ROX, and Bodipy-650 may be used. Four types of dNTPs whose 3' ends are modified with an ally group, which are modified with these different four fluorescent substances, may be used. At this time, the detection unit preferably includes, as light sources, Ar laser (488 nm), He—Ne laser (594.1 nm) and YAG laser (355 nm). The Ar laser is for excitation of Bodipy-FL-510 and R6G and the He—Ne laser is for excitation of ROX and Bodipy-650. The YAG laser is used for, after detection of fluorescence of the incorporated dNTP derivatives, returning the dNTP derivatives to an extendible state.

Exemplary steps of a stepwise elongation reaction are described below. A primer is hybridized to a single-stranded DNA template that is a biotin-modified target. Then Thermo Sequenase Reaction buffer, to which four types of dNTPs (3'-O-allyl-dGTP-PC-Bodipy-FL-510, 3'-O-allyl-dTTP-PC-R6G, 3'-O-allyl-dATP-PC-ROX, and 3'-O-allyl-dCTP-PC-Bodipy-650) which are labeled with different four fluorescent substances and whose 3' ends are modified with an ally group as well as Thermo Sequenase polymerase are added, is introduced into the flow cell from the injection port for an elongation reaction. The dNTP incorporated in the DNA template-primer complex has its 3' end modified with the allyl group, and so one or more bases are not incorporated in the DNA template-primer complex. After the elongation reaction, unreacted various types of dNTPs and polymerase are rinsed off by the buffer for cleaning. Then, the flow cell is irradiated with laser beams generated from the Ar laser light and the He—Ne laser at the same time. The irradiation with the laser beams excites the fluorescent substance labeling the dNTP incorporated in the DNA template-primer complex, and the fluorescence generated from the fluorescent substance is detected by the imaging device of the detection unit. The type of the base of the dNTP incorporated can be specified by specifying the wavelength of the fluorescence from the fluorescent substance labeling the dNTP captured in the DNA template-primer complex. Then, the flow cell is irradiated with laser light generated from the YAG laser, thus removing the fluorescent substance labeling the dNTP incorporated in the complex by optical cutting. Then, solution containing palladium is introduced into the passage, and the allyl group at the 3' end of the dNTP incorporated in the complex is transformed to a hydroxyl group by a palladium catalytic reaction. Such transformation of the allyl group at the 3' end to the hydroxyl group enables resumption of the elongation reaction of the DNA template-primer complex. After this catalytic reaction, the chamber is cleaned by the buffer for cleaning. This is repeatedly performed to determine the sequence of the immobilized single-stranded DNA template.

That is the description of the embodiment where the present invention is applied to a DNA sequencer. The present invention, however, is not limited to the application to a DNA sequencer, and is applicable generally to analyzers that are configured to sequentially inject reagents to a flow cell for analysis such as a biomolecular interaction analysis of small molecules, proteins, antigen antibody, hormone, bacteria and the like.

The present invention is not limited to the above-described embodiments, and may include various modification examples. For instance, the entire detailed configuration of the embodiments described above for explanatory convenience is not always necessary for the present invention. A part of one embodiment may be replaced with the configuration of another embodiment, or the configuration of one embodiment may be added to the configuration of another embodiment. The configuration of each embodiment may additionally include another configuration, or a part of the configuration may be deleted or replaced.

The above-described configurations, functions, processing parts, processing means and the like, a part or the entire of them, may be implemented by hardware by designing as an integrated circuit, for example. Alternatively, the above-described configurations, functions and the like may be implemented by software using a processor that interprets a program to implement these functions and executes the program. Information such as programs, tables and files to implement these functions may be placed on a recording device such as a memory, a hard disk or a SSD (Solid State Drive), or a recording medium such as an IC card, a SD card or a DVD.

REFERENCE SIGNS LIST

11 Reagent container
12 Reagent rack
13 Reagent rack base
14 Premixing container
15 Cover
16 Opening
17 Motor
18 Positioning pin
20 Sampling nozzle
21 Guide rail
22 Linear movement unit
23 Rotating shaft
24 Arm
30 Flow cell
31 Flow cell stage
32 Injection port
33 Discharge port
34 Passage
35 Sample immobilization layer
36 Upper substrate
37 Lower substrate
38 Spacer
40 Detection unit
41 Light source
42 Imaging device
50 Control/operation unit
51 Input unit
52 Display unit
53 Liquid level detection unit
60 Microsyringe
61 Plunger
62 First passage
63 Second passage
64 Cleaning liquid tank
65 Pump
66 Cleaning liquid circulation passage
67 Flow amount regulator
68 Cleaning tank
69 Waste liquid tank
71 First electromagnetic valve
72 Second electromagnetic valve
81 First cleaning liquid syringe
84 Second cleaning liquid syringe

The invention claimed is:

1. An analyzer, comprising:
a reagent rack installation part where a reagent rack holding a plurality of reagent containers is to be installed;
a flow cell installation part where a flow cell including an internal passage as well as an injection port and a discharge port connected to the internal passage is to be installed;
a sampling nozzle;
a liquid level detection unit that detects the sampling nozzle coming into contact with a liquid level;
a cleaning tank;
a nozzle driving mechanism that drives the sampling nozzle among the reagent containers, the cleaning tank and the injection port of the flow cell;
a detection unit that detects a change in a sample in the flow cell;
a solution sending system including: a cleaning liquid tank containing cleaning liquid; a microsyringe connected to the sampling nozzle, the microsyringe being for suction and ejection of liquid to/from a tip end of the sampling nozzle; a first valve to send cleaning liquid from the cleaning liquid tank to the microsyringe; and a second valve to send cleaning liquid from the cleaning liquid tank to the cleaning tank; and
a controller that controls various parts of the analyzer, wherein
the controller controls the microsyringe while inserting the sampling nozzle into a reagent by a predetermined distance in response to detection by the liquid level detection unit of a surface of the reagent in the reagent container, thus sucking a required amount of the reagent from the reagent container ahead of a part of the sampling nozzle filled with cleaning liquid, controls the microsyringe while inserting the sampling nozzle into the injection port of the flow cell, thus injecting the sucked reagent into the flow cell through the injection port, or operates the first valve and/or the second valve while positioning the sampling nozzle in the cleaning tank, thus cleaning an inside and/or an outside of the sampling nozzle.

2. The analyzer according to claim 1, further including a plurality of members enabling the liquid level detection unit to detect the sampling nozzle coming into contact as members to allow the nozzle driving mechanism to perform driving calibration of the sampling nozzle.

3. The analyzer according to claim 2, wherein
the nozzle driving mechanism includes: a guide rail; a movement unit that moves linearly along the guide rail; and an arm, to which the sampling nozzle is fixed, the arm rotating about a rotating shaft set at the movement unit, and
the members include at least two members that are disposed at a known interval in a direction along the guide rail, and at least two members that are disposed at a known interval in a direction orthogonal to the guide rail.

4. The analyzer according to claim 3, wherein
the controller has a function of calibration of a position of the sampling nozzle by detecting positions of the members using the liquid level detection unit, and the controller detects positions of at least two members disposed in the direction along the guide rail and finds, based on a driving signal to the nozzle driving mechanism and a distance between the two members, a linear movement coefficient that is a ratio between a traveling distance in the linear movement direction and the driving signal; detects a position of each of at least two members from two directions and finds, based on a driving signal to the nozzle driving mechanism and the linear movement coefficient, a rotating radius of a tip end of the sampling nozzle about the rotating shaft and a rotary movement coefficient that is a ratio of a rotating angle and the driving signal; and further detects two members disposed at a known interval in the direction orthogonal to the guide rail, and finds, based on a driving signal to the nozzle driving mechanism, the linear movement coefficient and the rotary movement coefficient, a rotating angle of the arm detecting the members.

5. The analyzer according to claim 4, wherein
when the found rotating radius of the tip end of the sampling nozzle is beyond a predetermined acceptable range, the controller stops driving of the sampling nozzle by the nozzle driving mechanism and announces abnormality.

6. The analyzer according to claim 1, wherein
a single-stranded DNA template is immobilized to the internal passage of the flow cell, and the analyzer functions as a DNA sequencer.

7. The analyzer according to claim 1, wherein
the nozzle driving mechanism includes: a guide rail; a movement unit that moves linearly along the guide rail; and an arm, to which the sampling nozzle is fixed, the arm rotating about a rotating shaft set at the movement unit, and
the arm has small rigidity such that, when the sampling nozzle is inserted into a tapered injection port of the flow cell, the arm itself bends, thus absorbing a positional error of the sampling nozzle due to the nozzle driving mechanism.

8. The analyzer according to claim 1, wherein
after finishing a reagent injection operation into the flow cell by the solution sending system while inserting the sampling nozzle into the injection port, the controller waits for predetermined duration and then controls the nozzle driving mechanism to remove the sampling nozzle from the injection port.

9. The analyzer according to claim 1, wherein
an amount of a reagent to be sucked from the reagent container to the sampling nozzle is capacity of the flow cell or more and an amount obtained by adding 10 µL to the capacity of the flow cell or less.

10. The analyzer according to claim 1, wherein
the solution sending system includes a cleaning liquid circulation passage, through which cleaning liquid in the cleaning liquid tank is sucked by a pump and is returned to the cleaning liquid tank again, and
the first valve includes a first electromagnetic valve provided in a passage connecting the cleaning liquid circulation passage and the microsyringe, and the second valve includes a second electromagnetic valve provided in a passage connecting the cleaning liquid circulation passage and the cleaning tank.

* * * * *